US008952018B2

(12) United States Patent
Dumble et al.

(10) Patent No.: US 8,952,018 B2
(45) Date of Patent: Feb. 10, 2015

(54) PHARMACEUTICAL COMBINATION OF MEK INHIBITOR AND B-RAF INHIBITORS

(71) Applicant: GlaxoSmithKline LLC, Philadelphia, PA (US)

(72) Inventors: Melissa Dumble, Collegeville, PA (US); Rakesh Kumar, Collegeville, PA (US); Sylvie Laquerre, Collegeville, PA (US); Peter Lebowitz, Collegeville, PA (US)

(73) Assignee: GlaxosmithKline LLC, Philadelphia`, PA (US)

( * ) Notice: Subject to any disclaimer, the term of this patent is extended or adjusted under 35 U.S.C. 154(b) by 0 days.

(21) Appl. No.: 14/197,421

(22) Filed: Mar. 5, 2014

(65) Prior Publication Data
US 2014/0187566 A1    Jul. 3, 2014

Related U.S. Application Data

(63) Continuation of application No. 13/499,779, filed as application No. PCT/US2010/052808 on Oct. 15, 2010, now Pat. No. 8,703,781.

(60) Provisional application No. 61/252,213, filed on Oct. 16, 2009.

(51) Int. Cl.
*A61K 31/506*    (2006.01)
*A61K 31/519*    (2006.01)
*A61K 45/06*    (2006.01)

(52) U.S. Cl.
CPC ............. *A61K 31/519* (2013.01); *A61K 31/506* (2013.01); *A61K 45/06* (2013.01)
USPC ................. 514/264.1; 514/341; 514/264.11; 546/274.1; 544/317; 544/331; 544/333; 544/279

(58) Field of Classification Search
CPC ............ A61K 2300/00; A61K 31/506; A61K 31/519; A61K 45/06; G01N 33/574; G01N 33/57419
USPC ............... 514/264.1, 341, 264.11; 546/274.1; 544/317, 331, 333, 279
See application file for complete search history.

(56) References Cited

U.S. PATENT DOCUMENTS 7,026,336 B1    4/2006    Dean et al.
2007/0244135 A1    10/2007    Hoelzemann et al.

FOREIGN PATENT DOCUMENTS

WO    2005121142 A1    12/2005
WO    2008120004 A1    10/2008
WO    WO2009137391    11/2009

OTHER PUBLICATIONS

PCT/US/2010/052808 Search Report dated Apr. 4, 2014.

*Primary Examiner* — Savitha Rao
(74) *Attorney, Agent, or Firm* — John Scott Young

(57) ABSTRACT

A novel combination comprising the MEK inhibitor N-{3-[3-cyclopropyl-5-(2-fluoro-4-iodo-phenylamino)6,8-dimethyl; -2,4,7-trioxo-3,4,6,7-tetrahydro-2H-pyrido[4,3-d]pyrimidin-1-yl]phenyl}acetamide, or a pharmaceutically acceptable salt or solvate thereof, with a B-Raf inhibitor, particularly N-{3-[5-(2-Amino-4-pyrimidinyl)-2-(1,1-dimethylethyl)-1,3-thiazol-4-yl]-2-fluorophenyl}-2,6-difluorobenzenesulfonamide or a pharmaceutically acceptable salt thereof, pharmaceutical compositions comprising the same and methods of using such combinations and compositions in the treatment of conditions in which the inhibition of MEK and/or B-Raf is beneficial, eg. cancer.

5 Claims, 2 Drawing Sheets

PHARMACEUTICAL COMBINATION OF MEK INHIBITOR AND B-RAF INHIBITORS

CROSS-REFERENCE TO RELATED APPLICATIONS

This application is filed as a continuation application of U.S. Ser. No. 13/499,779, filed Apr. 2, 2012, which is a National Phase Application of International Patent Application Serial No. PCT/US2010/052808 filed Oct. 15, 2010, which claims priority from 61,252,213 filed on Oct. 16, 2009 in the United States.

FIELD OF THE INVENTION

The present invention relates to a method of treating cancer in a mammal and to combinations useful in such treatment. In particular, the method relates to a novel combination comprising the MEK inhibitor N-{3-[3-cyclopropyl-5-(2-fluoro-4-iodo-phenylamino)6,8-dimethyl; -2,4,7-trioxo-3,4,6,7-tetrahydro-2H-pyrido[4,3-d]pyrimidin-1-yl]phenyl}acetamide, or a pharmaceutically acceptable salt or solvate thereof, with a B-Raf inhibitor, particularly N-{3-[5-(2-Amino-4-pyrimidinyl)-2-(1,1-dimethylethyl)-1,3-thiazol-4-yl]-2-fluorophenyl}-2,6-difluorobenzenesulfonamide or a pharmaceutically acceptable salt thereof, pharmaceutical compositions comprising the same and methods of using such combinations and compositions in the treatment of conditions in which the inhibition of MEK and/or B-Raf is beneficial, eg. cancer.

BACKGROUND OF THE INVENTION

Effective treatment of hyperproliferative disorders including cancer is a continuing goal in the oncology field. Generally, cancer results from the deregulation of the normal processes that control cell division, differentiation and apoptotic cell death and is characterized by the proliferation of malignant cells which have the potential for unlimited growth, local expansion and systemic metastasis. Deregulation of normal processes include abnormalities in signal transduction pathways and response to factors which differ from those found in normal cells.

An important large family of enzymes is the protein kinase enzyme family. Currently, there are about 500 different known protein kinases. Protein kinases serve to catalyze the phosphorylation of an amino acid side chain in various proteins by the transfer of the γ-phosphate of the ATP-Mg$^{2+}$ complex to said amino acid side chain. These enzymes control the majority of the signaling processes inside cells, thereby governing cell function, growth, differentiation and destruction (apoptosis) through reversible phosphorylation of the hydroxyl groups of serine, threonine and tyrosine residues in proteins.

Studies have shown that protein kinases are key regulators of many cell functions, including signal transduction, transcriptional regulation, cell motility, and cell division. Several oncogenes have also been shown to encode protein kinases, suggesting that kinases play a role in oncogenesis. These processes are highly regulated, often by complex intermeshed pathways where each kinase will itself be regulated by one or more kinases. Consequently, aberrant or inappropriate protein kinase activity can contribute to the rise of disease states associated with such aberrant kinase activity including benign and malignant proliferative disorders as well as diseases resulting from inappropriate activation of the immune and nervous systems. Due to their physiological relevance, variety and ubiquitousness, protein kinases have become one of the most important and widely studied family of enzymes in biochemical and medical research.

The protein kinase family of enzymes is typically classified into two main subfamilies: Protein Tyrosine Kinases and Protein Serine/Threonine Kinases, based on the amino acid residue they phosphorylate. The protein serine/threonine kinases (PSTK), includes cyclic AMP- and cyclic GMP-dependent protein kinases, calcium and phospholipid dependent protein kinase, calcium- and calmodulin-dependent protein kinases, casein kinases, cell division cycle protein kinases and others. These kinases are usually cytoplasmic or associated with the particulate fractions of cells, possibly by anchoring proteins. Aberrant protein serine/threonine kinase activity has been implicated or is suspected in a number of pathologies such as rheumatoid arthritis, psoriasis, septic shock, bone loss, many cancers and other proliferative diseases. Accordingly, serine/threonine kinases and the signal transduction pathways which they are part of are important targets for drug design. The tyrosine kinases phosphorylate tyrosine residues. Tyrosine kinases play an equally important role in cell regulation. These kinases include several receptors for molecules such as growth factors and hormones, including epidermal growth factor receptor, insulin receptor, platelet derived growth factor receptor and others. Studies have indicated that many tyrosine kinases are transmembrane proteins with their receptor domains located on the outside of the cell and their kinase domains on the inside. Much work is also in progress to identify modulators of tyrosine kinases as well.

Receptor tyrosine kinases (RTKs) catalyze phosphorylation of certain tyrosyl amino acid residues in various proteins, including themselves, which govern cell growth, proliferation and differentiation.

Downstream of the several RTKs lie several signaling pathways, among them is the Ras-Raf-MEK-ERK kinase pathway. It is currently understood that activation of Ras GTPase proteins in response to growth factors, hormones, cytokines, etc. stimulates phosphorylation and activation of Raf kinases. These kinases then phosphorylate and activate the intracellular protein kinases MEK1 and MEK2, which in turn phosphorylate and activate other protein kinases, ERK1 and 2. This signaling pathway, also known as the mitogen-activated protein kinase (MAPK) pathway or cytoplasmic cascade, mediates cellular responses to growth signals. The ultimate function of this is to link receptor activity at the cell membrane with modification of cytoplasmic or nuclear targets that govern cell proliferation, differentiation, and survival.

The constitutive activation of this pathway is sufficient to induce cellular transformation. Disregulated activation of the MAP kinase pathway due to aberrant receptor tyrosine kinase activation, Ras mutations or Raf mutations has frequently been found in human cancers, and represents a major factor determining abnormal growth control. In human malignances, Ras mutations are common, having been identified in about 30% of cancers. The Ras family of GTPase proteins (proteins which convert guanosine triphosphate to guanosine diphosphate) relay signals from activated growth factor receptors to downstream intracellular partners. Prominent among the targets recruited by active membrane-bound Ras are th Raf family of serine/threonine protein kinases. The Raf family is composed of three relarted kinases (A-, B- and C-Raf) that act as downstream effectors of Ras. Ras-medicated Raf activation in turn triggers activation of MEK1 and MEK2 (MAP/ERK kinases 1 and 2) which in turn phosphorylate ERK1 and ERK2 (extracellular signal-regulated kinases 1 and 2) on th tyrosine-185 and threonine-183. Activated ERK1 and ERK2 translocate and accumulate in the nucleus, where they can phosphorylate a variety of substrates, including transcription factors that control cellular growth and survival. Given the importance of the Ras/Raf/MEK/ERK pathway in the development of human cancers, the kinase components of the signaling cascade are merging as potentially important targets for the modulation of disease progression in cancer and other proliferative diseases.

MEK1 and MEK2 are members of a larger family of dual-specificity kinases (MEK1-7) that phosphorylate threonine and tyrosine residues of various MAP kinases. MEK1 and MEK2 are encoded by distinct genes, but they share high homology (80%) both within the C-terminal catalytic kinase domains and the most of the N-terminal regulatory region. Oncogenis forms of MEK1 and MEK2 have not been found in human cancers, but constitutive activation of MEK has been shown to result in cellular transformation. In addition to Raf, MEK can also be activated by other oncognese as well. So far, the only known substrates of MEK1 and MEK2 are ERK1 and ERK2. This unusual substrate specificity in addition to the unique ability to phosphorylate both tyrosine and threonine residues places MEK1 and MEK2 at a critical point in the signal transduction cascade which allows it to integrate many extracellular signals into the MAPK pathway.

Accordingly, it has been recognized that an inhibitor of a protein of the MAPK kinase pathway (eg. MEK) should be of value both as an anti-proliferative, pro-apoptotic and anti-invasive agent for use in the containment and/or treatment of proliferative or invasive disease.

Moreover, it is also known that a compound having MEK inhibitory activity effectively induces inhibition of ERK1/2 activity and suppression of cell proliferation (The Journal of Biological Chemistry, vol. 276, No. 4 pp. 2686-2692, 2001), and the compound is expected to show effects on diseases caused by undesirable cell proliferation, such as tumor genesis and/or cancer.

Mutations in various Ras GTPases and the B-Raf kinase have been identified that can lead to sustained and constitutive activation of the MAPK pathway, ultimately resulting in increased cell division and survival. As a consequence of this, these mutations have been strongly linked with the establishment, development, and progression of a wide range of human cancers. The biological role of the Raf kinases, and specifically that of B-Raf, in signal transduction is described in Davies, H., et al., *Nature* (2002) 9:1-6; Garnett, M. J. & Marais, R., *Cancer Cell* (2004) 6:313-319; Zebisch, A. & Troppmair, J., *Cell. Mol. Life. Sci.* (2006) 63:1314-1330; Midgley, R. S. & Kerr, D. J., *Crit. Rev. One/Hematol.* (2002) 44:109-120; Smith, R. A., et al., *Curr. Top. Med. Chem.* (2006) 6:1071-1089; and Downward, J., *Nat. Rev. Cancer* (2003) 3:11-22.

Naturally occurring mutations of the B-Raf kinase that activate MAPK pathway signaling have been found in a large percentage of human melanomas (Davies (2002) supra) and thyroid cancers (Cohen et al *J. Nat. Cancer Inst.* (2003) 95(8) 625-627 and Kimura et al *Cancer Res.* (2003) 63(7) 1454-1457), as well as at lower, but still significant, frequencies in the following:
Barret's adenocarcinoma (Garnett et al., *Cancer Cell* (2004) 6 313-319 and Sommerer et al *Oncogene* (2004) 23(2) 554-558), billiary tract carcinomas (Zebisch et al., *Cell. Mol. Life. Sci.* (2006) 63 1314-1330), breast cancer (Davies (2002) supra), cervical cancer (Moreno-Bueno et al *Clin. Cancer Res.* (2006) 12(12) 3865-3866), cholangiocarcinoma (Tannapfel et al *Gut* (2003) 52(5) 706-712), central nervous system tumors including primary CNS tumors such as glioblastomas, astrocytomas and ependymomas (Knobbe et al *Acta Neuropathol.* (Berl.) (2004) 108(6) 467-470, Davies (2002) supra, and Garnett et al., *Cancer Cell* (2004) supra) and secondary CNS tumors (i.e., metastases to the central nervous system of tumors originating outside of the central nervous system), colorectal cancer, including large intestinal colon carcinoma (Yuen et al *Cancer Res.* (2002) 62(22) 6451-6455, Davies (2002) supra and Zebisch et al., *Cell. Mol. Life. Sci.* (2006), gastric cancer (Lee et al *Oncogene* (2003) 22(44) 6942-6945), carcinoma of the head and neck including squamous cell carcinoma of the head and neck (Cohen et al *J. Nat. Cancer Inst.* (2003) 95(8) 625-627 and Weber et al *Oncogene* (2003) 22(30) 4757-4759), hematologic cancers including leukemias (Garnett et al., *Cancer Cell* (2004) supra, particularly acute lymphoblastic leukemia (Garnett et al., *Cancer Cell* (2004) supra and Gustafsson et al *Leukemia* (2005) 19(2) 310-312), acute myelogenous leukemia (AML) (Lee et al *Leukemia* (2004) 18(1) 170-172, and Christiansen et al *Leukemia* (2005) 19(12) 2232-2240), myelodysplastic syndromes (Christiansen et al *Leukemia* (2005) supra) and chronic myelogenous leukemia (Mizuchi et al *Biochem. Biophys. Res. Commun.* (2005) 326(3) 645-651); Hodgkin's lymphoma (Figl et al *Arch. Dermatol.* (2007) 143(4) 495-499), non-Hodgkin's lymphoma (Lee et al *Br. J. Cancer* (2003) 89(10) 1958-1960), megakaryoblastic leukemia (Eychene et al *Oncogene* (1995) 10(6) 1159-1165) and multiple myeloma (Ng et al *Br. J. Haematol.* (2003) 123(4) 637-645), hepatocellular carcinoma (Garnett et al., *Cancer Cell* (2004),
lung cancer (Brose et al *Cancer Res.* (2002) 62(23) 6997-7000, Cohen et al *J. Nat. Cancer Inst.* (2003) supra and Davies (2002) supra), including small cell lung cancer (Pardo et al *EMBO J.* (2006) 25(13) 3078-3088) and non-small cell lung cancer (Davies (2002) supra), ovarian cancer (Russell & McCluggage *J. Pathol.* (2004) 203(2) 617-619 and Davies (2002) supr), endometrial cancer (Garnett et al., *Cancer Cell* (2004) supra, and Moreno-Bueno et al *Clin. Cancer Res.* (2006) supra), pancreatic cancer (Ishimura et al *Cancer Lett.* (2003) 199(2) 169-173), pituitary adenoma (De Martino et al *J. Endocrinol. Invest.* (2007) 30(1) RC1-3), prostate cancer (Cho et al *Int. J. Cancer* (2006) 119(8) 1858-1862), renal cancer (Nagy et al *Int. J. Cancer* (2003) 106(6) 980-981), sarcoma (Davies (2002) supra), and skin cancers (Rodriguez-Viciana et al *Science* (2006) 311(5765) 1287-1290 and Davies (2002) supra). Overexpression of c-Raf has been linked to AML (Zebisch et al., *Cancer Res.* (2006) 66(7) 3401-3408, and Zebisch (*Cell. Mol. Life. Sci.* (2006)) and erythroleukemia (Zebisch et la., Cell. Mol. Life. Sci. (2006).

By virtue of the role played by the Raf family kinases in these cancers and exploratory studies with a range of preclinical and therapeutic agents, including one selectively targeted to inhibition of B-Raf kinase activity (King A. J., et al., (2006) *Cancer Res.* 66:11100-11105), it is generally accepted that inhibitors of one or more Raf family kinases will be useful for the treatment of such cancers or other condition associated with Raf kinase.

Mutation of B-Raf has also been implicated in other conditions, including cardio-facio cutaneous syndrome (Rodriguez-Viciana et al *Science* (2006) 311(5765) 1287-1290) and polycystic kidney disease (Nagao et al *Kidney Int.* (2003) 63(2) 427-437).

Though there have been many recent advances in the treatment of cancer with compounds such as the MEK and B-Raf inhibitors, there remains a need for more effective and/or enhanced treatment of an individual suffering the effects of cancer.

SUMMARY OF THE INVENTION

The present inventors have identified a combination of chemotherapeutic agents that provides increased activity over monotherapy. In particular, the drug combination that includes the MEK inhibitor N-{3-[3-cyclopropyl-5-(2-fluoro-4-iodo-phenylamino)6,8-dimethyl-2,4,7-trioxo-3,4,6,7-tetrahydro-2H-pyrido[4,3-d]pyrimidin-1-yl]phenyl}acetamide, or a pharmaceutically acceptable salt or solvate thereof, in combination with the B-Raf inhibitor N-{3-[5-(2-Amino-4-pyrimidinyl)-2-(1,1-dimethylethyl)-1,3-thiazol-4-yl]-2-fluorophenyl}-2,6-difluorobenzene-sulfonamide or a pharmaceutically acceptable salt thereof is described.

The MEK inhibitor of the invention is represented by the structure of formula (I):

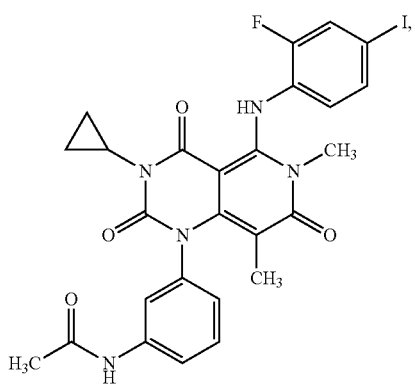

or a pharmaceutically acceptable salt or solvate thereof (collectively referred to herein as "compound A"), The B-Raf inhibitor of the invention is represented by the structure of formula (II):

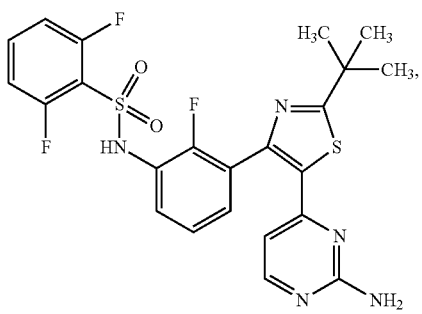

or a pharmaceutically acceptable salt thereof (collectively referred to herein as "compound B").

In a first aspect of the present invention, there is provided a combination comprising
(i) a compound of formula (I)):

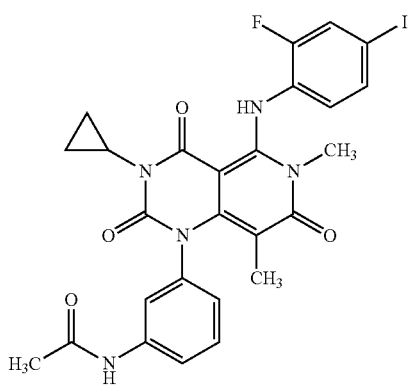

or a pharmaceutically acceptable salt or solvate thereof; and (ii) a compound of formula (II)

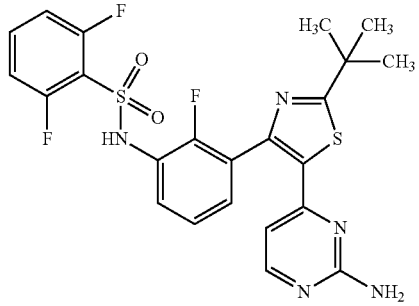

or a pharmaceutically acceptable salt thereof.

In another aspect of the invention, there is provided a combination comprising N-{3-[3-cyclopropyl-5-(2-fluoro-4-iodo-phenylamino)6,8-dimethyl-2,4,7-trioxo-3,4,6,7-tetrahydro-2H-pyrido[4,3-d]pyrimidin-1-yl]phenyl}acetamide dimethyl sulfoxide (solvate) and N-{3-[5-(2-Amino-4-pyrimidinyl)-2-(1,1-dimethylethyl)-1,3-thiazol-4-yl]-2-fluorophenyl}-2,6-difluorobenzenesulfonamide methanesulfonate.

In another aspect of the present invention, there is provided a combination, comprising:
(i) a compound of formula (I):

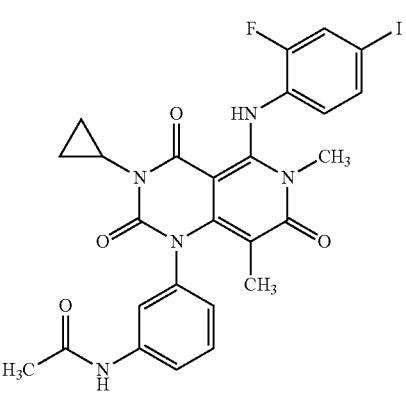

or a pharmaceutically acceptable salt or solvate thereof; and
(ii) a compound of formula (II):

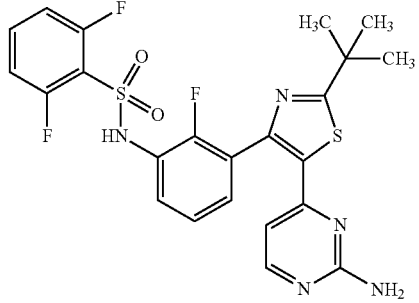

or a pharmaceutically acceptable salt thereof for use in therapy.

In another aspect of the present invention, there is provided a combination, comprising:

(i) a compound of formula (I):

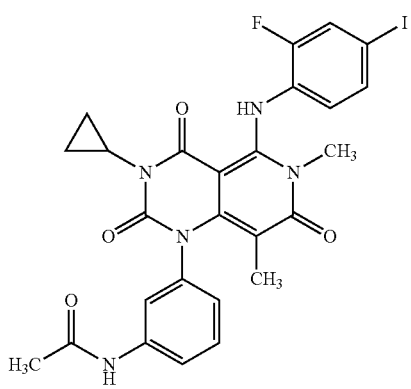 [SMILES: CC(=O)Nc1cccc(-n2c(=O)n(C3CC3)c(=O)c3c(Nc4ccc(I)cc4F)n(C)c(=O)c(C)c32)c1]

(I)

or a pharmaceutically acceptable salt or solvate thereof; and (ii) a compound of formula (II):

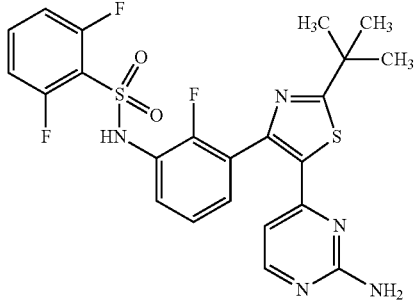

(II)

or a pharmaceutically acceptable salt thereof for use in the treatment of cancer.

In another aspect of the present invention, there is provided a pharmaceutical composition, comprising:

(i) a compound of formula (I):

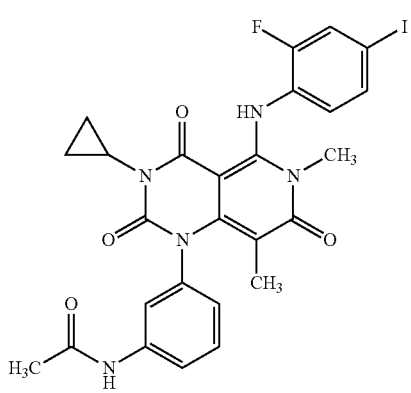

(I)

or a pharmaceutically acceptable salt or solvate thereof; and (ii) a compound of formula (II):

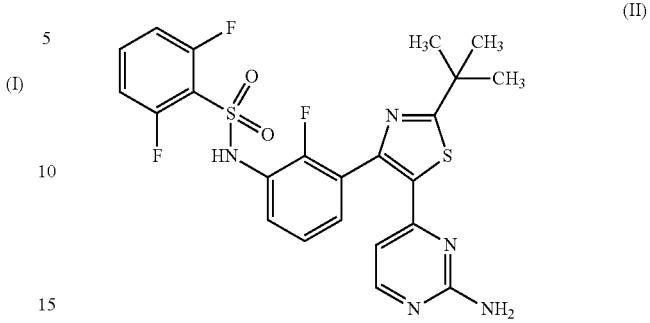

(II)

or a pharmaceutically acceptable salt thereof together with a pharmaceutically acceptable diluent or carrier.

In a another aspect there is provided the use of a combination comprising i) a compound of formula (I)

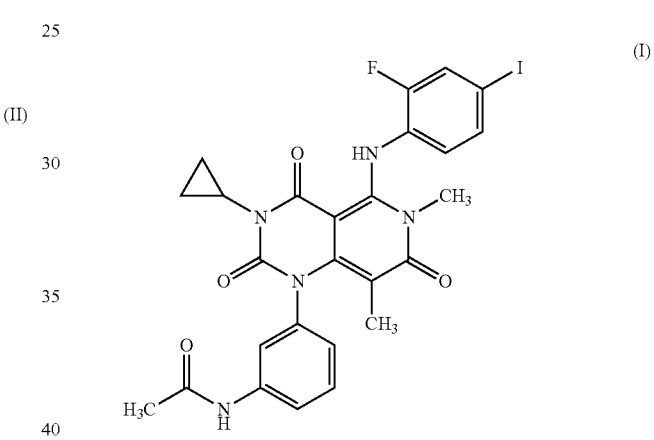

(I)

or a pharmaceutically acceptable salt or solvate thereof; and (ii) a compound of formula (II):

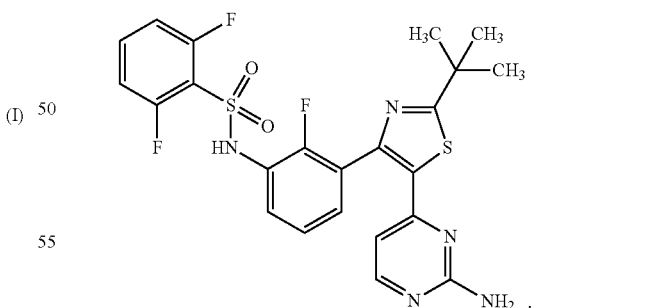

(II)

or a pharmaceutically acceptable salt thereof in the manufacture of a medicament for the treatment of cancer.

In another aspect there is provided a method of treatment of cancer in a mammal comprising administering to said mammal:

(i) a therapeutically effective amount of a compound of formula (I)

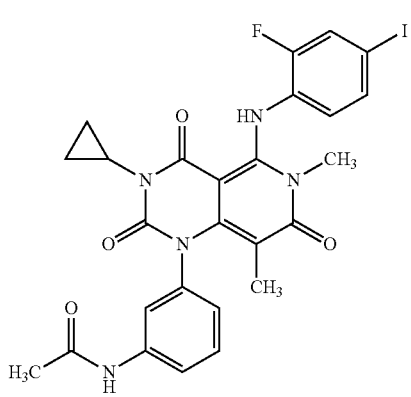

or a pharmaceutically acceptable salt or solvate thereof: and (ii) a compound of formula (II):

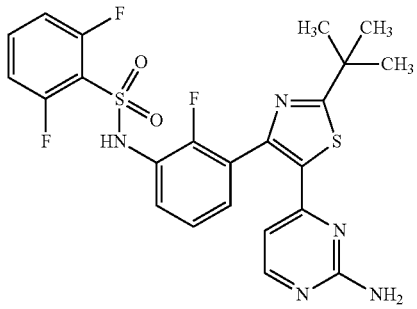

or a pharmaceutically acceptable salt thereof.

In another aspect, there is provided a method of treating cancer in a human in need thereof comprising the administration of a therapeutically effective amount of a combination of N-{3-[3-cyclopropyl-5-(2-fluoro-4-iodo-phenylamino)6,8-dimethyl-2,4,7-trioxo-3,4,6,7-tetrahydro-2H-pyrido[4,3-d]pyrimidin-1-yl]phenyl}acetamide, or a pharmaceutically acceptable salt or solvate thereof, and N-{3-[5-(2-Amino-4-pyrimidinyl)-2-(1,1-dimethylethyl)-1,3-thiazol-4-yl]-2-fluorophenyl}-2,6-difluorobenzenesulfonamide or a pharmaceutically acceptable salt thereof.

In another aspect, there is provided a method of treating cancer in a human in need thereof comprising the administration of a therapeutically effective amount of a combination of N-{3-[3-cyclopropyl-5-(2-fluoro-4-iodo-phenylamino)6,8-dimethyl-2,4,7-trioxo-3,4,6,7-tetrahydro-2H-pyrido[4,3-d]pyrimidin-1-yl]phenyl}acetamide dimethyl sulfoxide solvate and N-{3-[5-(2-Amino-4-pyrimidinyl)-2-(1,1-dimethylethyl)-1,3-thiazol-4-yl]-2-fluorophenyl}-2,6-difluorobenzenesulfonamide methanesulfonate.

In a further aspect of this invention is provided a method of treating cancer in a mammal in need thereof which comprises administering a therapeutically effective amount of a combination of the invention wherein the combination is administered within a specific period and for a duration of time.

DETAILED DESCRIPTION OF THE INVENTION

Figure 1:
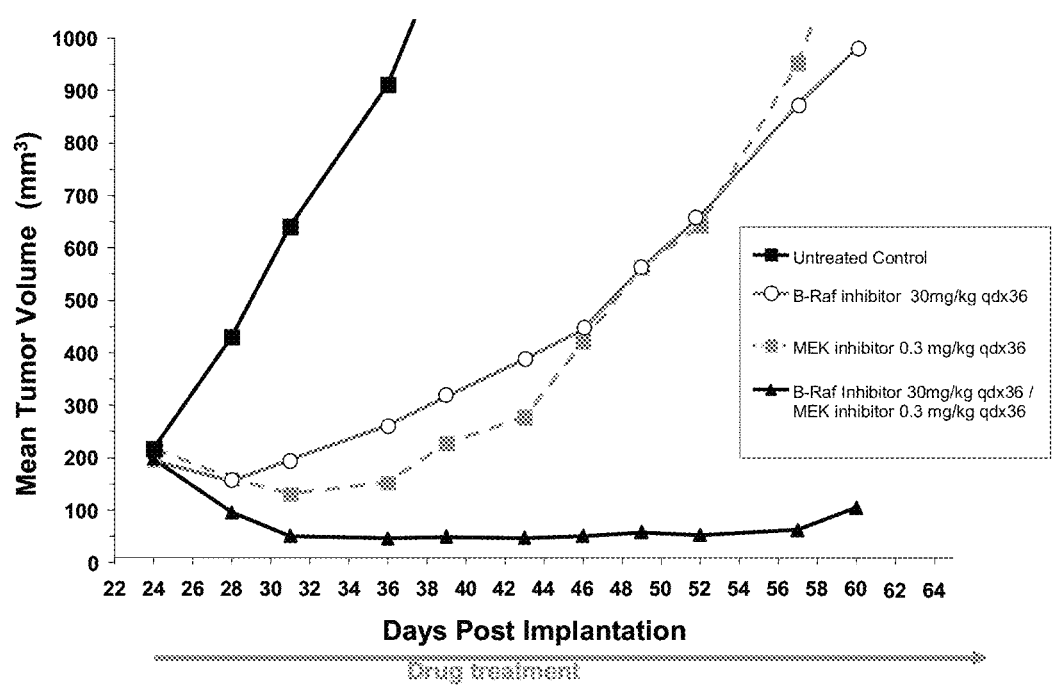
FIG. 1 is a graph showing the tumor growth inhibition due to administration of the MEK inhibitor of Compound A, the B-Raf inhibitor of Compound B, and the combination thereof.

As used herein, the MEK inhibitor N-{3-[3-cyclopropyl-5-(2-fluoro-4-iodo-phenylamino)6,8-dimethyl-2,4,7-trioxo-3,4,6,7-tetrahydro-2H-pyrido[4,3-d]pyrimidin-1-yl]phenyl}acetamide, or a pharmaceutically acceptable salt or solvate thereof, is represented by a compound of formula (I):

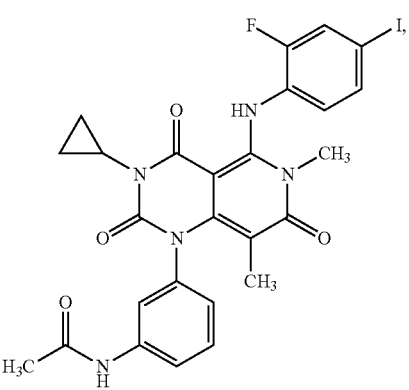

or pharmaceutically acceptable salt or solvate thereof. For convenience, the group of possible compound and salts or solvates is collectively referred to as Compound A, meaning that reference to Compound A will refer to any of the compound or pharmaceutically acceptable salt or solvate thereof in the alternative.

Depending on naming convention, the compound of formula (I) may also properly be referred to as N-{3-[3-cyclopropyl-5-[(2-fluoro-4-iodophenyl)amino]-6,8-dimethyl-2,4,7-trioxo-3,4,6,7-tetrahydropyrido[4,3-d]pyrimidin-1(2H)-yl]phenyl}acetamide.

As used herein, the BRaf inhibitor N-{3-[5-(2-Amino-4-pyrimidinyl)-2-(1,1-dimethylethyl)-1,3-thiazol-4-yl]-2-fluorophenyl}-2,6-difluorobenzenesulfonamide or pharmaceutically acceptable salt thereof, is represented by a compound formula (II):

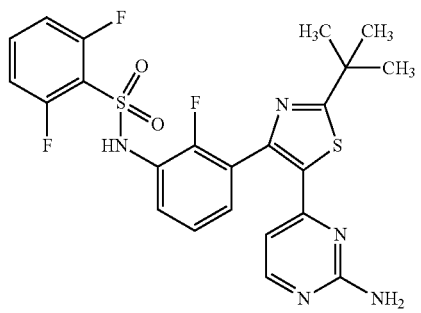 [SMILES: CC(C)(C)c1nc(-c2cccc(NS(=O)(=O)c3c(F)cccc3F)c2F)c(-c2ccnc(N)n2)s1]

or a pharmaceutically acceptable salt thereof, For convenience, the group of possible compound and salts is collectively referred to as Compound B, meaning that reference to Compound B will refer to any of the compound or pharmaceutically acceptable salt thereof in the alternative.

As used herein the term "combination of the invention" refers to a combination comprising Compound A and Compound B.

As used herein the term "neoplasm" refers to an abnormal growth of cells or tissue and is understood to include benign, i.e., non-cancerous growths, and malignant, i.e., cancerous growths. The term "neoplastic" means of or related to a neoplasm.

As used herein the term "agent" is understood to mean a substance that produces a desired effect in a tissue, system, animal, mammal, human, or other subject. Accordingly, the term "anti-neoplastic agent" is understood to mean a substance producing an anti-neoplastic effect in a tissue, system, animal, mammal, human, or other subject. It is also to be understood that an "agent" may be a single compound or a combination or composition of two or more compounds.

By the term "treating" and derivatives thereof as used herein, is meant therapeutic therapy. In reference to a particular condition, treating means: (1) to ameliorate the condition or one or more of the biological manifestations of the condition, (2) to interfere with (a) one or more points in the biological cascade that leads to or is responsible for the condition or (b) one or more of the biological manifestations of the condition (3) to alleviate one or more of the symptoms, effects or side effects associated with the condition or one or more of the symptoms, effects or side effects associated with the condition or treatment thereof, or (4) to slow the progression of the condition or one or more of the biological manifestations of the condition.

As used herein, "prevention" is understood to refer to the prophylactic administration of a drug to substantially diminish the likelihood or severity of a condition or biological manifestation thereof, or to delay the onset of such condition or biological manifestation thereof. The skilled artisan will appreciate that "prevention" is not an absolute term. Prophylactic therapy is appropriate, for example, when a subject is considered at high risk for developing cancer, such as when a subject has a strong family history of cancer or when a subject has been exposed to a carcinogen.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Compounds A and/or B may contain one or more chiral atoms, or may otherwise be capable of existing as enantiomers. Accordingly, the compounds of this invention include mixtures of enantiomers as well as purified enantiomers or enantiomerically enriched mixtures. Also, it is understood that all tautomers and mixtures of tautomers are included within the scope of Compound A and Compound B.

Also, it is understood that compounds A and B may be presented, separately or both, as solvates. As used herein, the term "solvate" refers to a complex of variable stoichiometry formed by a solute (in this invention, compounds of formula (I) or (II) or a salt thereof and a solvent. Such solvents for the purpose of the invention may not interfere with the biological activity of the solute. Examples of suitable solvents include, but are not limited to, water, methanol, dimethylsulforide. ethanol and acetic acid. In one embodiment, the solvent used is a pharmaceutically acceptable solvent. Examples of suitable pharmaceutically acceptable solvents include, without limitation, water, ethanol and acetic acid. In another embodiment, the solvent used is water.

Compounds A and B may have the ability to crystallize in more than one form, a characteristic, which is known polymorphism, and it is understood that such polymorphic forms ("polymorphs") are within the scope of Compounds A and B. Polymorphism generally can occur as a response to changes in temperature or pressure or both and can also result from variations in the crystallization process. Polymorphs can be distinguished by various physical characteristics known in the art such as x-ray diffraction patterns, solubility, and melting point.

Compound A is disclosed and claimed, along with pharmaceutically acceptable salts thereof, and also as solvates thereof, as being useful as an inhibitor of MEK activity, particularly in treatment of cancer, in WO 2005/121142. Compound A is the compound of Example 4-1. Compound A can be prepared as described in WO 2005/121142.

Suitably, Compound A is in the form of a dimethyl sulfoxide solvate. Suitably, Compound A is in the form of a sodium salt. Suitably, Compound A is in the form of a solvate selected from: hydrate, acetic acid, ethanol, nitromethane, chlorobenzene, 1-pentancol, isopropyl alcohol, ethylene glycol and 3-methyl-1-butanol. These solvates and salt forms can be prepared by one of skill in the art from the description in WO 2005/121142. Compound B is disclosed and claimed, along with pharmaceutically acceptable salts thereof, as being useful as an inhibitor of BRaf activity, particularly in the treatment of cancer, in PCT patent application PCT/US09/42682. Compound B is embodied by Examples 58a through 58e of the application. The PCT application was published on 12 Nov. 2009 as publication WO2009/137391, and is hereby incorporated by reference.

More particularly, Compound B may be prepared according to the methods below:

Method 1: Compound B (first crystal form)-N-{3-[5-(2-Amino-4-pyrimidinyl)-2-(1,1-dimethylethyl)-1,3-thiazol-4-yl]-2-fluorophenyl}-2,6-difluorobenzene-sulfonamide

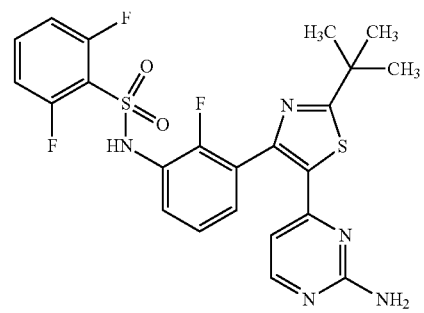

A suspension of N-{3-[5-(2-chloro-4-pyrimidinyl)-2-(1,1-dimethylethyl)-1,3-thiazol-4-yl]-2-fluorophenyl}-2,6-difluorobenzenesulfonamide (196 mg, 0.364 mmol) and ammonia in methanol 7M (8 ml, 56.0 mmol) was heated in a sealed tube to 90° C. for 24 h. The reaction was diluted with DCM and added silica gel and concentrated. The crude product was chromatographed on silica gel eluting with 100% DCM to 1:1 [DCM:(9:1 EtOAc:MeOH)]. The clean fractions were concentrated to yield the crude product. The crude product was repurified by reverse phase HPLC (a gradient of acetonitrile: water with 0.1% TFA in both). The combined clean fractions were concentrated then partitioned between DCM and saturated NaHCO$_3$. The DCM layer was separated and dried over Na$_2$SO$_4$. The title compound, N-{3-[5-(2-amino-4-pyrimidinyl)-2-(1,1-dimethylethyl)-1,3-thiazol-4-yl]-2-fluorophenyl}-2,6-difluorobenzenesulfonamide was obtained (94 mg, 47% yield). $^1$H NMR (400 MHz, DMSO-d$_6$) δ ppm 10.83 (s, 1 H), 7.93 (d, J=5.2 Hz, 1 H), 7.55-7.70 (m, 1 H), 7.35-7.43 (m, 1 H), 7.31 (t, J=6.3 Hz, 1 H), 7.14-7.27 (m, 3 H), 6.70 (s, 2 H), 5.79 (d, J=5.13 Hz, 1 H), 1.35 (s, 9 H). MS (ESI): 519.9 [M+H]$^+$.

Method 2: Compound B (alternative crystal form)-N-{3-[5-(2-Amino-4-pyrimidinyl)-2-(1,1-dimethylethyl)-1,3-thiazol-4-yl]-2-fluorophenyl}-2,6-difluorobenzenesulfonamide 19.6 mg of N-{3-[5-(2-Amino-4-pyrimidinyl)-2-(1,1-dimethylethyl)-1,3-thiazol-4-yl]-2-fluorophenyl}-2,6-difluorobenzenesulfonamide (may be prepared in accordance with example 58a) was combined with 500 L of ethyl acetate in a 2-mL vial at room temperature. The slurry was temperature-cycled between 0-40° C. for 48 hrs. The resulting slurry was allowed to cool to room temperature and the solids were collected by vacuum filtration. The solids were analyzed by Raman, PXRD, DSC/TGA analyses, which indicated a crystal form different from the crystal form resulting from Example 58a, above.

Method 3: Compound B (alternative crystal form, large batch)-N-{3-[5-(2-amino-4-pyrimidinyl)-2-(1,1-dimethylethyl)-1,3-thiazol-4-yl]-2-fluorophenyl}-2,6-difluorobenzenesulfonamide

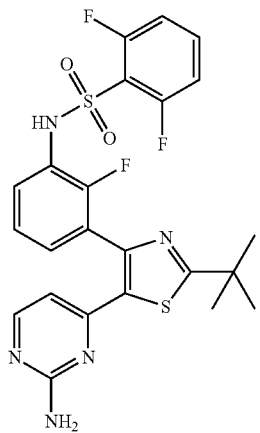 [SMILES: CC(C)(C)c1nc(-c2cccc(NS(=O)(=O)c3c(F)cccc3F)c2F)c(-c2ccnc(N)n2)s1]

Step A: methyl 3-{[(2,6-difluorophenyl)sulfonyl]amino}-2-fluorobenzoate

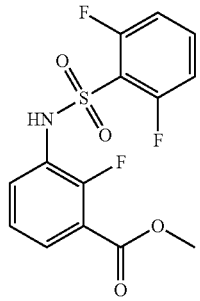 [SMILES: COC(=O)c1cccc(NS(=O)(=O)c2c(F)cccc2F)c1F]

Methyl 3-amino-2-fluorobenzoate (50 g, 1 eq) was charged to reactor followed by dichloromethane (250 mL, 5 vol). The contents were stirred and cooled to −15° C. and pyridine (26.2 mL, 1.1 eq) was added. After addition of the pyridine, the reactor contents were adjusted to −15° C. and the addition of 2,6-difluororobenzenesulfonyl chloride (39.7 mL, 1.0 eq) was started via addition funnel. The temperature during addition was kept <25° C. After complete addition, the reactor contents were warmed to 20-25° C. and held overnight. Ethyl acetate (150 mL) was added and dichloromethane was removed by distillation. Once distillation was complete, the reaction mixture was then diluted once more with ethyl acetate (5 vol) and concentrated. The reaction mixture was diluted with ethyl acetate (10 vol) and water (4 vol) and the contents heated to 50-55° C. with stirring until all solids dissolve. The layers were settled and separated. The organic layer was diluted with water (4 vol) and the contents heated to 50-55° for 20-30 min. The layers were settled and then separated and the ethyl acetate layer was evaporated under reduced pressure to ~3 volumes. Ethyl Acetate (5 vol.) was added and again evaporated under reduced pressure to ~3 volumes. Cyclohexane (9 vol) was then added to the reactor and the contents were heated to reflux for 30 min then cooled to 0° C. The solids were filtered and rinsed with cyclohexane (2×100 mL). The solids were air dried overnight to obtain methyl 3-{[(2,6-difluorophenyl)sulfonyl]amino}-2-fluorobenzoate (94.1 g, 91%).

Step B: N-{3-[(2-chloro-4-pyrimidinyl)acetyl]-2-fluorophenyl}-2,6-difluorobenzenesulfonamide

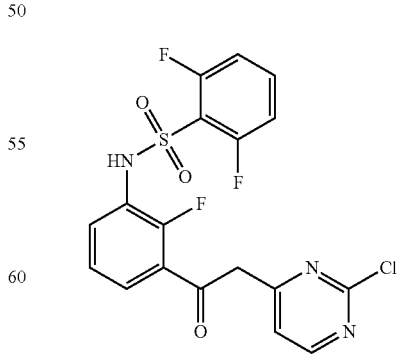

Methyl 3-{[(2,6-difluorophenyl)sulfonyl]amino}-2-fluorobenzoate (490 g, 1 equiv.), prepared generally in accordance with Step A, above, was dissolved in THF (2.45 L, 5 vols) and stirred and cooled to 0-3° C. 1M lithium bis(trimethylsilyl)amide in THF (5.25 L, 3.7 equiv.) solution was charged to the reaction mixture followed addition of 2-chloro-4-methylpyrimidine (238 g, 1.3 equiv.) in THF (2.45 L, 5 vols). The reaction was then stirred for 1 hr. The reaction was quenched with 4.5M HCl (3.92 L, 8 vols). The aqueous layer (bootom layer) was removed and discarded. The organic layer was concentrated under reduced pressure to ~2 L. IPAC (isopropyl acetate) (2.45 L) was added to the reaction mixture which was then concentrated to ~2 L. IPAC (0.5 L) and MTBE (2.45 L) was added and stirred overnight under $N_2$. The solids were filtered. The solids and mother filtrate added back together and stirred for several hours. The solids were filtered and washed with MTBE (~5 vol). The solids were placed in vacuum oven at 50° C. overnight. The solids were dried in vacuum oven at 30° C. over weekend to obtain N-{3-[(2-chloro-4-pyrimidinyl)acetyl]-2-fluorophenyl}-2,6-difluorobenzenesulfonamide (479 g, 72%).

Step C: N-{3-[5-(2-chloro-4-pyrimidinyl)-2-(1,1-dimethylethyl)-1,3-thiazol-4-yl]-2-fluorophenyl}-2,6-difluorobenzenesulfonamide

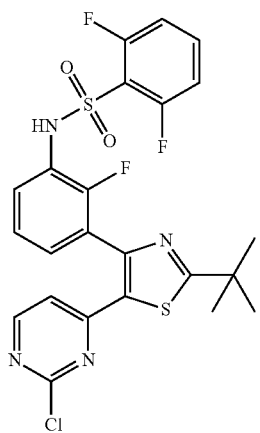 [SMILES: CC(C)(C)c1nc(-c2cccc(NS(=O)(=O)c3c(F)cccc3F)c2F)c(-c2ccnc(Cl)n2)s1]

To a reactor vessel was charged N-{3-[(2-chloro-4-pyrimidinyl)acetyl]-2-fluorophenyl}-2,6-difluorobenzenesulfonamide (30 g, 1 eq) followed by dichloromethane (300 mL). The reaction slurry was cooled to –10° C. and N-bromosuccinimide ("NBS") (12.09 g, 1 eq) was added in 3 approximately equal portions, stirring for 10-15 minutes between each addition. After the final addition of NBS, the reaction mixture was warmed to ~20° C. and stirred for 45 min. Water (5 vol) was then added to the reaction vessel and the mixture was stirred and then the layers separated. Water (5 vol) was again added to the dichloromethane layer and the mixture was stirred and the layers separated. The dichloromethane layers were concentrated to –120 mL. Ethyl acetate (7 vol) was added to the reaction mixture and concentrated to ~120 mL. Dimethylacetamide (270 mL) was then added to the reaction mixture and cooled to ~10° C. 2,2-Dimethylpropanethioamide (1.3 g, 0.5 eq) in 2 equal portions was added to the reactor contents with stirring for ~5 minutes between additions. The reaction was warmed to 20-25° C. After 45 min, the vessel contents were heated to 75° C. and held for 1.75 hours. The reaction mixture was then cooled to 5° C. and water (270 ml) was slowly charged keeping the temperature below 30° C. Ethyl acetate (4 vol) was then charged and the mixture was stirred and layers separated. Ethyl acetate (7 vol) was again charged to the aqueous layer and the contents were stirred and separated. Ethyl acetate (7 vol) was charged again to the aqueous layer and the contents were stirred and separated. The organic layers were combined and washed with water (4 vol) 4 times and stirred overnight at 20-25° C. The organic layers were then concentrated under heat and vacuum to 120 mL. The vessel contents were then heated to 50° C. and heptanes (120 mL) were added slowly. After addition of heptanes, the vessel contents were heated to reflux then cooled to 0° C. and held for ~2 hrs. The solids were filtered and rinsed with heptanes (2×2 vol). The solid product was then dried under vacuum at 30° C. to obtain N-{3-[5-(2-chloro-4-pyrimidinyl)-2-(1,1-dimethylethyl)-1,3-thiazol-4-yl]-2-fluorophenyl}-2,6-difluorobenzenesulfonamide (28.8 g, 80%).

Step D: N-{3-[5-(2-amino-4-pyrimidinyl)-2-(1,1-dimethylethyl)-1,3-thiazol-4-yl]-2-fluorophenyl}-2,6-difluorobenzenesulfonamide In 1 gal pressure reactor, a mixture of N-{3-[5-(2-chloro-4-pyrimidinyl)-2-(1,1-dimethylethyl)-1,3-thiazol-4-yl]-2-fluorophenyl}-2,6-difluorobenzenesulfonamide (120 g) prepared in accordance with Step C, above, and ammonium hydroxide (28-30%, 2.4 L, 20 vol) was heated in the sealed pressure reactor to 98-103° C. and stirred at this temperature for 2 hours. The reaction was cooled slowly to room temperature (20° C.) and stirred overnight. The solids were filtered and washed with minimum amount of the mother liquor and dried under vacuum. The solids were added to a mixture of EtOAc (15 vol)/water (2 vol) and heated to complete dissolution at 60-70° C. and the aqueous layer was removed and discarded. The EtOAC layer was charged with water (1 vol) and neutralized with aq. HCl to ~pH 5.4-5.5. and added water (1-vol). The aqueous layer was removed and discarded at 60-70° C. The organic layer was washed with water (1 vol) at 60-70° C. and the aqueous layer was removed and discarded. The organic layer was filtered at 60° C. and concentrated to 3 volumes. EtOAc (6 vol) was charged into the mixture and heated and stirred at 72° C. for 10 min, then cooled to 20° C. and stirred overnight. EtOAc was removed via vacuum distillation to concentrate the reaction mixture to ~3 volumes. The reaction mixture was maintained at ~65-70° C. for ~30 mins. Product crystals having the same crystal form as those prepared in Example 58b (and preparable by the procedure of Example 58b), above, in heptanes slurry were charged. Heptane (9 vol) was slowly added at 65-70° C. The slurry was stirred at 65-70° C. for 2-3 hours and then cooled slowly to 0-5° C. The product was filtered, washed with EtOAc/heptane (3/1 v/v, 4 vol) and dried at 45° C. under vacuum to obtain N-{3-[5-(2-amino-4-pyrimidinyl)-2-(1,1-dimethylethyl)-1,3-thiazol-4-yl]-2-fluorophenyl}-2,6-difluorobenzenesulfonamide (102.3 g, 88%).

Method 4: Compound B (mesylate salt)-N-{3-[5-(2-amino-4-pyrimidinyl)-2-(1,1-dimethylethyl)-1,3-thiazol-4-yl]-2-fluorophenyl}-2,6-difluorobenzenesulfonamide methanesulfonate

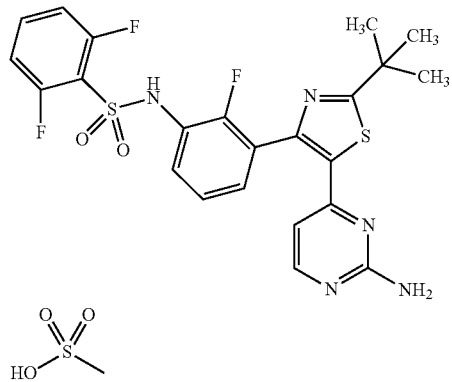

To a solution of N-{3-[5-(2-amino-4-pyrimidinyl)-2-(1,1-dimethylethyl)-1,3-thiazol-4-yl]-2-fluorophenyl}-2,6-difluorobenzenesulfonamide (204 mg, 0.393 mmol) in isopropanol (2 mL), methanesulfonic acid (0.131 mL, 0.393 mmol) was added and the solution was allowed to stir at room temperature for 3 hours. A white precipitate formed and the slurry was filtered and rinsed with diethyl ether to give the title product as a white crystalline solid (210 mg, 83% yield). $^1$H NMR (400 MHz, DMSO-d6) δ ppm 10.85 (s, 1 H) 7.92-8.05 (m, 1 H) 7.56-7.72 (m, 1 H) 6.91-7.50 (m, 7 H) 5.83-5.98 (m, 1 H) 2.18-2.32 (m, 3 H) 1.36 (s, 9 H). MS (ESI): 520.0 [M+H].

Method 5: Compound B (alternative mesylate salt embodiment)-N-{3-[5-(2-amino-4-pyrimidinyl)-2-(1,1-dimethylethyl)-1,3-thiazol-4-yl]-2-fluorophenyl}-2,6-difluorobenzenesulfonamide methanesulfonate N-{3-[5-(2-amino-4-pyrimidinyl)-2-(1,1-dimethylethyl)-1,3-thiazol-4-yl]-2-fluorophenyl}-2,6-difluorobenzenesulfonamide (as may be prepared according to example 58a) (2.37 g, 4.56 mmol) was combined with pre-filtered acetonitrile (5.25 vol, 12.4 mL). A pre-filtered solution of mesic acid (1.1 eq., 5.02 mmol, 0.48 g) in H$_2$O (0.75 eq., 1.78 mL) was added at 20° C. The temperature of the resulting mixture was raised to 50-60° C. while maintaining a low agitation speed. Once the mixture temperature reached to 50-60° C., a seed slurry of N-{3-[5-(2-amino-4-pyrimidinyl)-2-(1,1-dimethylethyl)-1,3-thiazol-4-yl]-2-fluorophenyl}-2,6-difluorobenzenesulfonamide methanesulfonate (1.0% w/w slurried in 0.2 vol of pre-filtered acetonitrile) was added, and the mixture was aged while agitating at a speed fast enough to keep solids from settling at 50-60° C. for 2 hr. The mixture was then cooled to 0-5° C. at 0.25° C./min and held at 0-5° C. for at 6 hr. The mixture was filtered and the wet cake was washed twice with pre-filtered acetonitrile. The first wash consisted of 14.2 ml (6 vol) pre-filtered acetonitrile and the second wash consisted of 9.5 ml (4 vol) pre-filtered acetonitrile. The wet solid was dried at 50° C. under vacuum, yielding 2.39 g (85.1% yield) of product.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in a compound of the present invention. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, which are not pharmaceutically acceptable, may be useful in the preparation of compounds of this invention and these form a further aspect of the invention. Salts may be readily prepared by a person skilled in the art.

While it is possible that, for use in therapy, compounds A and B, may be administered as the raw chemical, it is possible to present the active ingredient as a pharmaceutical composition. Accordingly, the invention further provides pharmaceutical compositions, which include a compound A and/or a compound B, and one or more pharmaceutically acceptable carriers, diluents, or excipients. The compounds A and B are as described above. The carrier(s), diluent(s) or excipient(s) must be acceptable in the sense of being compatible with the other ingredients of the formulation, capable of pharmaceutical formulation, and not deleterious to the recipient thereof. In accordance with another aspect of the invention there is also provided a process for the preparation of a pharmaceutical composition including admixing a Compound A and/or Compound B, with one or more pharmaceutically acceptable carriers, diluents or excipients. Such elements of the pharmaceutical compositions utilized may be presented in separate pharmaceutical combinations or formulated together in one pharmaceutical composition. Accordingly, the invention further provides a combination of pharmaceutical compositions one of which includes Compound A and one or more pharmaceutically acceptable carriers, diluents, or excipients and a pharmaceutical composition containing Compound B and one or more pharmaceutically acceptable carriers, diluents, or excipients.

Compound A and Compound B are as described above and may be utilized in any of the compositions described above.

Pharmaceutical compositions may be presented in unit dose forms containing a predetermined amount of active ingredient per unit dose. As is known to those skilled in the art, the amount of active ingredient per dose will depend on the condition being treated, the route of administration and the age, weight and condition of the patient. Preferred unit dosage compositions are those containing a daily dose or sub-dose, or an appropriate fraction thereof, of an active ingredient. Furthermore, such pharmaceutical compositions may be prepared by any of the methods well known in the pharmacy art.

Compounds A and B may be administered by any appropriate route. Suitable routes include oral, rectal, nasal, topical (including buccal and sublingual), vaginal, and parenteral (including subcutaneous, intramuscular, intravenous, intradermal, intrathecal, and epidural). It will be appreciated that the preferred route may vary with, for example, the condition of the recipient of the combination and the cancer to be treated. It will also be appreciated that each of the agents administered may be administered by the same or different routes and that the Compounds A and B may be compounded together in a pharmaceutical composition.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also to granulating, the powder mixture can be run through the tablet machine and the result is imperfectly formed slugs broken into granules. The granules can be lubricated be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to prevent sticking to the tablet forming dies by means of the addition of stearic acid, a stearate salt, talc or mineral oil. The lubricated mixture is then compressed into tablets. The compounds of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, compositions for oral administration can be microencapsulated. The composition can also be prepared to prolong or sustain the release as for example by coating or embedding particulate material in polymers, wax or the like.

The agents for use according to the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Agents for use according to the present invention may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or as enemas.

Pharmaceutical compositions adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions adapted for administration by inhalation include fine particle dusts or mists that may be generated by means of various types of metered dose pressurised aerosols, nebulizers or insufflators.

Pharmaceutical compositions adapted for vaginal administration may be presented as pessaries, tampons, creams, gels, pastes, foams or spray compositions.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the compositions may include other agents conventional in the art having regard to the type of formulation in question, for example those suitable for oral administration may include flavoring agents. Unless otherwise defined, in all dosing protocols described herein, the regimen of compounds administered does not have to commence with the start of treatment and terminate with the end of treatment, it is only required that the number of consecutive days in which both compounds are administered and the optional number of consecutive days in which only one of the component compounds is administered, or the indicated dosing protocol—including the amount of compound administered, occur at some point during the course of treatment.

Compounds A and B may be employed in combination in accordance with the invention by administration simultaneously in a unitary pharmaceutical composition including both compounds. Alternatively, the combination may be administered separately in separate pharmaceutical compositions, each including one of the compounds A and B in a sequential manner wherein, for example, Compound A or Compound B is administered first and the other second. Such sequential administration may be close in time (eg. simultaneously) or remote in time. Furthermore, it does not matter if the compounds are administered in the same dosage form, e.g. one compound may be administered topically and the other compound may be administered orally. Suitably, both compounds are administered orally.

Thus in one embodiment, one or more doses of Compound A are administered simultaneously or separately with one or more doses of Compound B.

Unless otherwise defined, in all dosing protocols described herein, the regimen of compounds administered does not have to commence with the start of treatment and terminate with the end of treatment, it is only required that the number of consecutive days in which both compounds are administered and the optional number of consecutive days in which only one of the component compounds is administered, or the indicated dosing protocol—including the amount of compound administered, occur at some point during the course of treatment.

In one embodiment, multiple doses of Compound A are administered simultaneously or separately with multiple doses of Compound B.

In one embodiment, multiple doses of Compound A are administered simultaneously or separately with one dose of Compound B.

In one embodiment, one dose of Compound A is administered simultaneously or separately with multiple doses of Compound B.

In one embodiment one dose of Compound A is administered simultaneously or separately with one dose of Compound B.

In all the above embodiments Compound A may be administered first or Compound B may be administered first.

The combinations may be presented as a combination kit. By the term "combination kit" "or kit of parts" as used herein is meant the pharmaceutical composition or compositions that are used to administer Compound A and Compound B according to the invention. When both compounds are administered simultaneously, the combination kit can contain Compound A and Compound B in a single pharmaceutical composition, such as a tablet, or in separate pharmaceutical compositions. When Compounds A and B are not administered simultaneously, the combination kit will contain Compound A and Compound B in separate pharmaceutical compositions either in a single package or Compound A and Compound B in separate pharmaceutical compositions in separate packages.

In one aspect there is provided a kit of parts comprising components:
Compound A in association with a pharmaceutically acceptable excipients, diluents or carrier; and
Compound B in association with a pharmaceutically acceptable excipients, diluents or carrier.

In one embodiment of the invention the kit of parts comprising the following components:
Compound A in association with a pharmaceutically acceptable excipients, diluents or carrier; and
Compound B in association with a pharmaceutically acceptable excipients, diluents or carrier,
wherein the components are provided in a form which is suitable for sequential, separate and/or simultaneous administration.

In one embodiment the kit of parts comprises:
a first container comprising Compound A in association with a pharmaceutically acceptable excipient, diluent or carrier; and
a second container comprising Compound B in association with a pharmaceutically acceptable excipient, diluent or carrier, and a container means for containing said first and second containers.

The combination kit can also be provided by instruction, such as dosage and administration instructions. Such dosage and administration instructions can be of the kind that are provided to a doctor, for example by a drug product label, or they can be of the kind that are provided by a doctor, such as instructions to a patient.

The term "loading dose" as used herein will be understood to mean a single dose or short duration regimen of Compound A or Compound B having a dosage higher than the maintenance dose administered to the subject to, for example, rapidly increase the blood concentration level of the drug. Suitably, a short duration regimen for use herein will be from: 1 to 14 days; suitably from 1 to 7 days; suitably from 1 to 3 days; suitably for three days; suitably for two days; suitably for one day. In some embodiments, the "loading dose" can increase the blood concentration of the drug to a therapeutically effective level. In some embodiments, the "loading dose" can increase the blood concentration of the drug to a therapeutically effective level in conjunction with a maintenance dose of the drug. The "loading dose" can be administered once per day, or more than once per day (e.g., up to 4 times per day). Suitably the "loading dose" will be administered once a day. Suitably, the loading dose will be an amount from 2 to 100 times the maintenance dose; suitably from 2 to 10 times; suitably from 2 to 5 times; suitably 2 times; suitably 3 times; suitably 4 times; suitably 5 times. Suitably, the loading dose will be administered for from 1 to 7 days; suitably from 1 to 5 days; suitably from 1 to 3 days; suitably for 1 day; suitably for 2 days; suitably for 3 days, followed by a maintenance dosing protocol.

The term "maintenance dose" as used herein will be understood to mean a dose that is serially administered (for example; at least twice), and which is intended to either slowly raise blood concentration levels of the compound to a therapeutically effective level, or to maintain such a therapeutically effective level. The maintenance dose is generally administered once per day and the daily dose of the maintenance dose is lower than the total daily dose of the loading dose.

Suitably the combinations of this invention are administered within a "specified period".

By the term "specified period" and derivatives thereof, as used herein is meant the interval of time between the administration of one of Compound A and Compound B and the other of Compound A and Compound B. Unless otherwise defined, the specified period can include simultaneous administration. When both compounds of the invention are administered once a day the specified period refers to administration of Compound A and Compound B during a single day. When one or both compounds of the invention are administered more than once a day, the specified period is calculated based on the first administration of each compound on a specific day. All administrations of a compound of the invention that are subsequent to the first during a specific day are not considered when calculating the specific period.

Suitably, if the compounds are administered within a "specified period" and not administered simultaneously, they are both administered within about 24 hours of each other—in this case, the specified period will be about 24 hours; suitably they will both be administered within about 12 hours of each other—in this case, the specified period will be about 12 hours; suitably they will both be administered within about 11 hours of each other—in this case, the specified period will be about 11 hours; suitably they will both be administered within about 10 hours of each other—in this case, the specified period will be about 10 hours; suitably they will both be administered within about 9 hours of each other—in this case, the specified period will be about 9 hours; suitably they will both be administered within about 8 hours of each other—in this case, the specified period will be about 8 hours; suitably they will both be administered within about 7 hours of each other—in this case, the specified period will be about 7 hours; suitably they will both be administered within about 6 hours of each other—in this case, the specified period will be about 6 hours; suitably they will both be administered within about 5 hours of each other—in this case, the specified period will be about 5 hours; suitably they will both be administered within about 4 hours of each other—in this case, the specified period will be about 4 hours; suitably they will both be administered within about 3 hours of each other—in this case, the specified period will be about 3 hours; suitably they will be administered within about 2 hours of each other—in this case, the specified period will be about 2 hours; suitably they will both be administered within about 1 hour of each other—in this case, the specified period will be about 1 hour. As used herein, the administration of Compound A and Compound B in less than about 45 minutes apart is considered simultaneous administration.

Suitably, when the combination of the invention is administered for a "specified period", the compounds will be co-administered for a "duration of time".

By the term "duration of time" and derivatives thereof, as used herein is meant that both compounds of the invention are administered for an indicated number of consecutive days.

Regarding "specified period" administration: Suitably, both compounds will be administered within a specified period for at least one day—in this case, the duration of time will be at least one day; suitably, during the course to treatment, both compounds will be administered within a specified period for at least 3 consecutive days—in this case, the duration of time will be at least 3 days; suitably, during the course to treatment, both compounds will be administered within a specified period for at least 5 consecutive days—in this case, the duration of time will be at least 5 days; suitably, during the course to treatment, both compounds will be administered within a specified period for at least 7 consecutive days—in this case, the duration of time will be at least 7 days; suitably, during the course to treatment, both compounds will be administered within a specified period for at least 14 consecutive days—in this case, the duration of time will be at least 14 days; suitably, during the course to treatment, both compounds will be administered within a specified period for at least 30 consecutive days—in this case, the duration of time will be at least 30 days.

Further regarding "specified period" administration:

Suitably, during the course of treatment, Compound A and Compound B will be administered within a specified period for from 1 to 4 days over a 7 day period, and during the other days of the 7 day period Compound A will be administered alone. Suitably, this 7 day protocol is repeated for 2 cycles or for 14 days; suitably for 4 cycles or 28 days; suitably for continuous administration.

Suitably, during the course of treatment, Compound A and Compound B will be administered within a specified period for from 1 to 4 days over a 7 day period, and during the other days of the 7 day period Compound B will be administered alone. Suitably, this 7 day protocol is repeated for 2 cycles or for 14 days; suitably for 4 cycles or 28 days; suitably for continuous administration. Suitably, Compound B is administered for consecutive days during the 7 day period. Suitably, Compound B is administered in a pattern of every other day during each 7 day period.

Suitably, during the course of treatment, Compound A and Compound B will be administered within a specified period for 3 days over a 7 day period, and during the other days of the 7 day period Compound B will be administered alone. Suitably, this 7 day protocol is repeated for 2 cycles or for 14 days; suitably for 4 cycles or 28 days; suitably for continuous administration. Suitably, Compound A will be administered 3 consecutive days during the 7 day period.

Suitably, during the course of treatment, Compound A and Compound B will be administered within a specified period for 2 days over a 7 day period, and during the other days of the 7 day period Compound B will be administered alone. Suitably, this 7 day protocol is repeated for 2 cycles or for 14 days; suitably for 4 cycles or 28 days; suitably for continuous administration. Suitably, Compound A will be administered 2 consecutive days during the 7 day period.

Suitably, during the course of treatment, Compound A and Compound B will be administered within a specified period for 1 day during a 7 day period, and during the other days of the 7 day period Compound B will be administered alone. Suitably, this 7 day protocol is repeated for 2 cycles or for 14 days; suitably for 4 cycles or 28 days; suitably for continuous administration.

Suitably, if the compounds are not administered during a "specified period", they are administered sequentially. By the term "sequential administration", and derivates thereof, as used herein is meant that one of Compound A and Compound B is administered for two or more consecutive days and the other of Compound A and Compound B is subsequently administered for two or more consecutive days. Also, contemplated herein is a drug holiday utilized between the sequential administration of one of Compound A and Compound B and the other of Compound A and Compound B. As used herein, a drug holiday is a period of days after the sequential administration of one of Compound A and Compound B and before the administration of the other of Compound A and Compound B where neither Compound A nor Compound B is administered. Suitably the drug holiday will be a period of days selected from: 1 day, 2 days, 3 days, 4 days, 5 days, 6 days, 7 days, 8 days, 9 days, 10 days, 11 days, 12 days, 13 days and 14 days.

Regarding sequential administration:
Suitably, one of Compound A and Compound B is administered for from 1 to 30 consecutive days, followed by an optional drug holiday, followed by administration of the other of Compound A and Compound B for from 1 to 30 consecutive days. Suitably, one of Compound A and Compound B is administered for from 2 to 21 consecutive days, followed by an optional drug holiday, followed by administration of the other of Compound A and Compound B for from 2 to 21 consecutive days. Suitably, one of Compound A and Compound B is administered for from 2 to 14 consecutive days, followed by a drug holiday of from 1 to 14 days, followed by administration of the other of Compound A and Compound B for from 2 to 14 consecutive days. Suitably, one of Compound A and Compound B is administered for from 3 to 7 consecutive days, followed by a drug holiday of from 3 to 10 days, followed by administration of the other of Compound A and Compound B for from 3 to 7 consecutive days.

Suitably, Compound B will be administered first in the sequence, followed by an optional drug holiday, followed by administration of Compound A. Suitably, Compound B is administered for from 1 to 21 consecutive days, followed by an optional drug holiday, followed by administration of Compound A for from 1 to 21 consecutive days. Suitably, Compound B is administered for from 3 to 21 consecutive days, followed by a drug holiday of from 1 to 14 days, followed by administration of Compound A for from 3 to 21 consecutive days. Suitably, Compound B is administered for from 3 to 21 consecutive days, followed by a drug holiday of from 3 to 14 days, followed by administration of Compound A for from 3 to 21 consecutive days. Suitably, Compound B is administered for 21 consecutive days, followed by an optional drug holiday, followed by administration of Compound A for 14 consecutive days. Suitably, Compound B is administered for 14 consecutive days, followed by a drug holiday of from 1 to 14 days, followed by administration of Compound A for 14 consecutive days. Suitably, Compound B is administered for 7 consecutive days, followed by a drug holiday of from 3 to 10 days, followed by administration of Compound A for 7 consecutive days. Suitably, Compound B is administered for 3 consecutive days, followed by a drug holiday of from 3 to 14 days, followed by administration of Compound A for 7 consecutive days. Suitably, Compound B is administered for 3 consecutive days, followed by a drug holiday of from 3 to 10 days, followed by administration of Compound A for 3 consecutive days.

Suitably, Compound A will be administered first in the sequence, followed by an optional drug holiday, followed by administration of Compound B. Suitably, Compound A is administered for from 1 to 21 consecutive days, followed by an optional drug holiday, followed by administration of Compound B for from 1 to 21 consecutive days. Suitably, Compound A is administered for from 3 to 21 consecutive days, followed by a drug holiday of from 1 to 14 days, followed by administration of Compound B for from 3 to 21 consecutive days. Suitably, Compound A is administered for from 3 to 21 consecutive days, followed by a drug holiday of from 3 to 14 days, followed by administration of Compound B for from 3 to 21 consecutive days. Suitably, Compound A is administered for 21 consecutive days, followed by an optional drug holiday, followed by administration of Compound B for 14 consecutive days. Suitably, Compound A is administered for 14 consecutive days, followed by a drug holiday of from 1 to 14 days, followed by administration of Compound B for 14 consecutive days. Suitably, Compound A is administered for 7 consecutive days, followed by a drug holiday of from 3 to 10 days, followed by administration of Compound B for 7 consecutive days. Suitably, Compound A is administered for 3 consecutive days, followed by a drug holiday of from 3 to 14 days, followed by administration of Compound B for 7 consecutive days. Suitably, Compound A is administered for 3 consecutive days, followed by a drug holiday of from 3 to 10 days, followed by administration of Compound B for 3 consecutive days.

It is understood that a "specified period" administration and a "sequential" administration can be followed by repeat dosing or can be followed by an alternate dosing protocol, and a drug holiday may precede the repeat dosing or alternate dosing protocol.

Suitably, the amount of Compound A (based on weight of unsalted/unsolvated amount) administered as part of the combination according to the present invention will be an amount selected from about 0.125 mg to about 10 mg; suitably, the amount will be selected from about 0.25 mg to about 9 mg; suitably, the amount will be selected from about 0.25 mg to about 8 mg; suitably, the amount will be selected from about 0.5 mg to about 8 mg; suitably, the amount will be selected from about 0.5 mg to about 7 mg; suitably, the amount will be selected from about 1 mg to about 7 mg; suitably, the amount will be about 5 mg. Accordingly, the amount of Compound A administered as part of the combination according to the present invention will be an amount selected from about 0.125 mg to about 10 mg. For example, the amount of Compound A administered as part of the combination according to the present invention can be 0.125 mg, 0.25 mg, 0.5 mg, 0.75 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg.

Suitably, the amount of Compound B (based on weight of unsalted/unsolvated amount) administered as part of the combination according to the present invention will be an amount selected from about 10 mg to about 600 mg. Suitably, the amount will be selected from about 30 mg to about 300 mg; suitably, the amount will be selected from about 30 mg to about 280 mg; suitably, the amount will be selected from about 40 mg to about 260 mg; suitably, the amount will be selected from about 60 mg to about 240 mg; suitably, the amount will be selected from about 80 mg to about 220 mg; suitably, the amount will be selected from about 90 mg to about 210 mg; suitably, the amount will be selected from about 100 mg to about 200 mg, suitably, the amount will be selected from about 110 mg to about 190 mg, suitably, the amount will be selected from about 120 mg to about 180 mg, suitably, the amount will be selected from about 130 mg to about 170 mg, suitably, the amount will be selected from about 140 mg to about 160 mg, suitably, the amount will be 150 mg. Accordingly, the amount of Compound B administered as part of the combination according to the present invention will be an amount selected from about 10 mg to about 300 mg. For example, the amount of Compound B administered as part of the combination according to the present invention is suitably selected from 10 mg, 20 mg, 30 mg, 40 mg, 50 mg, 60 mg, 70 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg and 300 mg. Suitably, the selected amount of Compound B is administered from 1 to 4 times a day. Suitably, the selected amount of Compound B is administered twice a day. Suitably, Compound B is administered at an amount of 150 mg twice a day. Suitably, the selected amount of Compound B is administered once a day.

As used herein, all amounts specified for Compound A and Compound B are indicated as the amount of free or unsalted compound.

Method of Treatment

The combinations of the invention, are believed to have utility in disorders wherein the inhibition of MEK and/or B-Raf is beneficial.

The present invention thus also provides a combination of the invention, for use in therapy, particularly in the treatment of disorders wherein the inhibition of MEK and/or B-Raf activity is beneficial, particularly cancer.

A further aspect of the invention provides a method of treatment of a disorder wherein to inhibition of MEK and/or B-Raf is beneficial, comprising administering a combination of the invention.

A further aspect of the present invention provides the use of a combination of the invention in the manufacture of a medicament for the treatment of a disorder wherein the inhibition of MEK and/or B-Raf is beneficial.

Typically, the disorder is a cancer such that inhibition of MEK and/or B-Raf has a beneficial effect. Examples of cancers that are suitable for treatment with combination of the invention include, but are limited to, both primary and metastatic forms of head and neck, breast, lung, colon, ovary, and prostate cancers. Suitably the cancer is selected from: brain (gliomas), glioblastomas, astrocytomas, glioblastoma multiforme, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, ovarian, pancreatic, prostate, sarcoma, osteosarcoma, giant cell tumor of bone, thyroid cancer, lymphoblastic T cell leukemia, Chronic myelogenous leukemia, Chronic lymphocytic leukemia, Hairy-cell leukemia, acute lymphoblastic leukemia, acute myelogenous leukemia, AML, Chronic neutrophilic leukemia, Acute lymphoblastic T cell leukemia, plasmacytoma, Immunoblastic large cell leukemia, Mantle cell leukemia, Multiple myeloma Megakaryoblastic leukemia, multiple myeloma, acute megakaryocytic leukemia, promyelocytic leukemia, Erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, lung cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

Additionally, examples of a cancer to be treated include Barret's adenocarcinoma; billiary tract carcinomas; breast cancer; cervical cancer; cholangiocarcinoma; central nervous system tumors including primary CNS tumors such as glioblastomas, astrocytomas (e.g., glioblastoma multiforme) and ependymomas, and secondary CNS tumors (i.e., metastases to the central nervous system of tumors originating outside of the central nervous system); colorectal cancer including large intestinal colon carcinoma; gastric cancer; carcinoma of the head and neck including squamous cell carcinoma of the head and neck; hematologic cancers including leukemias and lymphomas such as acute lymphoblastic leukemia, acute myelogenous leukemia (AML), myelodysplastic syndromes, chronic myelogenous leukemia, Hodgkin's lymphoma, non-Hodgkin's lymphoma, megakaryoblastic leukemia, multiple myeloma and erythroleukemia; hepatocellular carcinoma; lung cancer including small cell lung cancer and non-small cell lung cancer; ovarian cancer; endometrial cancer; pancreatic cancer; pituitary adenoma; prostate cancer; renal cancer; sarcoma; skin cancers including melanomas; and thyroid cancers.

Suitably, the present invention relates to a method for treating or lessening the severity of a cancer selected from: brain (gliomas), glioblastomas, Bannayan-Zonana syndrome, Cowden disease, Lhermitte-Duclos disease, breast, colon, head and neck, kidney, lung, liver, melanoma, ovarian, pancreatic, prostate, sarcoma and thyroid.

Suitably, the present invention relates to a method for treating or lessening the severity of a cancer selected from ovarian, breast, pancreatic and prostate.

The combination of the invention may be used alone or in combination with one or more other therapeutic agents. The invention thus provides in a further aspect a further combination comprising a combination of the invention with a further therapeutic agent or agents, compositions and medicaments comprising the combination and use of the further combination, compositions and medicaments in therapy, in particular in the treatment of diseases susceptible to inhibition of MEK and/or kinase B.

In the embodiment, the combination of the invention may be employed with other therapeutic methods of cancer treatment. In particular, in anti-neoplastic therapy, combination therapy with other chemotherapeutic, hormonal, antibody agents as well as surgical and/or radiation treatments other than those mentioned above are envisaged. Combination therapies according to the present invention thus include the administration of Compound A and Compound B as well as optional use of other therapeutic agents including other anti-neoplastic agents. Such combination of agents may be administered together or separately and, when administered separately this may occur simultaneously or sequentially in any order, both close and remote in time. In one embodiment, the pharmaceutical combination includes Compound A and Compound B, and optionally at least one additional anti-neoplastic agent.

As indicated, therapeutically effective amounts of Compound A and Compound B are discussed above. The therapeutically effective amount of the further therapeutic agents of the present invention will depend upon a number of factors including, for example, the age and weight of the mammal, the precise condition requiring treatment, the severity of the condition, the nature of the formulation, and the route of administration. Ultimately, the therapeutically effective amount will be at the discretion of the attendant physician or veterinarian. The relative timings of administration will be selected in order to achieve the desired combined therapeutic effect.

In one embodiment, the further anti-cancer therapy is surgical and/or radiotherapy.

In one embodiment, the further anti-cancer therapy is at least one additional anti-neoplastic agent.

Any anti-neoplastic agent that has activity versus a susceptible tumor being treated may be utilized in the combination. Typical anti-neoplastic agents useful include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and antifolate compounds; topoisomerase I inhibitors such as camptothecins; hormones and hormonal analogues; signal transduction pathway inhibitors; non-receptor tyrosine angiogenesis inhibitors; immunotherapeutic agents; proapoptotic agents; and cell cycle signaling inhibitors.

Anti-microtubule or anti-mitotic agents: Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2/M$ phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. Paclitaxel has been approved for clinical use in the treatment of refractory ovarian cancer in the United States (Markman et al., Yale Journal of Biology and Medicine, 64:583, 1991; McGuire et al., Ann. Intem, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide. 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine,N-tert-butyl ester, 13-ester with 5β-20-epoxy-1,2α,4,7β,10β, 13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C"-norvincaleuko-blastine [R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes: Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, oxaliplatin, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer.

Carboplatin, platinum, diammine [1,1-cyclobutane-dicarboxylate(2-)-O,O'], is commercially available as PARAPLATIN® as an injectable solution. Carboplatin is primarily indicated in the first and second line treatment of advanced ovarian carcinoma.

Alkylating agents: Alkylating agents are non-phase anticancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease.

Busulfan, 1,4-butanediol dimethanesulfonate, is commercially available as MYLERAN® TABLETS. Busulfan is indicated for the palliative treatment of chronic myelogenous leukemia.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease.

Antibiotic anti-neoplastics: Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas.

Topoisomerase II inhibitors: Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children.

Antimetabolite neoplastic agents: Antimetabolite neoplastic agents are phase specific anti-neoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine).

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Other purine analogs include pentostatin, erythrohydroxynonyladenine, fludarabine phosphate, and cladribine.

Gemcitabine, 2'-deoxy-2',2'-difluorocytidine monohydrochloride (R-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer.

Methotrexate, N-[4-[(2,4-diamino-6-pteridinyl)methyl]methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder.

Topoisomerase I inhibitors: Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®. Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer.

Hormones and hormonal analogues: Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagagonists such as goserelin acetate and luprolide.

Signal transduction pathway inhibitors: Signal transduction pathway inhibitors are those inhibitors, which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, ret, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S, and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-lacaci, L., et al, Int. J. Cancer (2000), 88(1), 44-52.

Inhibitors of Phosphotidyl inositol-3 Kinase family members including blockers of PI3-kinase, ATM, DNA-PK, and Ku are also useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also useful in the present invention are Myo-inositol signaling inhibitors such as phospholipase C blockers and Myo-inositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer:erbB Family Receptor Tyrosine Kinases, Breast cancer Res., 2000, 2(3), 176-183); and 2CB VEGFR2 specific antibody (see Brekken, R. A. et al, Selective Inhibition of VEGFR2Activity by a monoclonal Anti-VEGF antibody blocks tumor growth in mice, Cancer Res. (2000) 60, 5117-5124).

Anti-angiogenic agents: Anti-angiogenic agents including non-receptorMEKngiogenesis inhibitors may alo be useful. Anti-angiogenic agents such as those which inhibit the effects of vascular edothelial growth factor, (for example the anti-vascular endothelial cell growth factor antibody bevacizumab [Avastin™], and compounds that work by other mechanisms (for example linomide, inhibitors of integrin αvβ3 function, endostatin and angiostatin);

Immunotherapeutic agents: Agents used in immunotherapeutic regimens may also be useful in combination with the compounds of formula (I). Immunotherapy approaches, including for example ex-vivo and in-vivo approaches to increase the immunogenecity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies Proapoptotoc agents: Agents used in proapoptotic regimens (e.g., bcl-2 antisense oligonucleotides) may also be used in the combination of the present invention.

Cell cycle signalling inhibitors: Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2): 215-230.

In one embodiment, the combination of the present invention comprises a compound of formula I or a salt or solvate thereof and at least one anti-neoplastic agent selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine MEKngiogenesis inhibitors, immunotherapeutic agents, proapoptotic agents, and cell cycle signaling inhibitors.

In one embodiment, the combination of the present invention comprises a compound of formula I or a salt or solvate thereof and at least one anti-neoplastic agent which is an anti-microtubule agent selected from diterpenoids and vinca alkaloids.

In a further embodiment, the at least one anti-neoplastic agent agent is a diterpenoid.

In a further embodiment, the at least one anti-neoplastic agent is a vinca alkaloid.

In one embodiment, the combination of the present invention comprises a compound of formula I or a salt or solvate thereof and at least one anti-neoplastic agent, which is a platinum coordination complex.

In a further embodiment, the at least one anti-neoplastic agent is paclitaxel, carboplatin, or vinorelbine.

In a further embodiment, the at least one anti-neoplastic agent is carboplatin.

In a further embodiment, the at least one anti-neoplastic agent is vinorelbine.

In a further embodiment, the at least one anti-neoplastic agent is paclitaxel.

In one embodiment, the combination of the present invention comprises a compound of formula I and salts or solvates thereof and at least one anti-neoplastic agent which is a signal transduction pathway inhibitor.

In a further embodiment the signal transduction pathway inhibitor is an inhibitor of a growth factor receptor kinase VEGFR2, TIE2, PDGFR, BTK, erbB2, EGFr, IGFR-1, TrkA, TrkB, TrkC, or c-fms. In a further embodiment the signal transduction pathway inhibitor is an inhibitor of a serine/threonine kinase rafk, akt, or PKC-zeta.

In a further embodiment the signal transduction pathway inhibitor is an inhibitor of a non-receptor tyrosine kinase selected from the src family of kinases.

In a further embodiment the signal transduction pathway inhibitor is an inhibitor of c-src.

In a further embodiment the signal transduction pathway inhibitor is an inhibitor of Ras oncogene selected from inhibitors of farnesyl transferase and geranylgeranyl transferase.

In a further embodiment the signal transduction pathway inhibitor is an inhibitor of a serine/threonine kinase selected from the group consisting of PI3K.

In a further embodiment the signal transduction pathway inhibitor is a dual EGFr/erbB2 inhibitor, for example N-{3-Chloro-4-[(3-fluorobenzyl)oxy]phenyl}-6-[5-({[2-(methanesulphonyl)ethyl]amino}methyl)-2-furyl]-4-quinazolinamine (structure below):

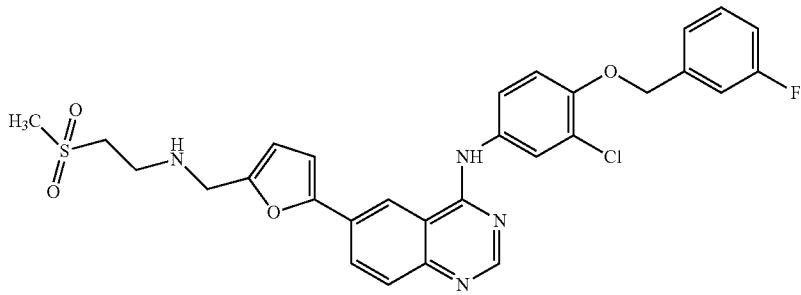 [SMILES: CS(=O)(=O)CCNCc1ccc(-c2ccc3ncnc(Nc4ccc(OCc5cccc(F)c5)c(Cl)c4)c3c2)o1]

In one embodiment, the combination of the present invention comprises a compound of formula I or a salt or solvate thereof and at least one anti-neoplastic agent which is a cell cycle signaling inhibitor.

In further embodiment, cell cycle signaling inhibitor is an inhibitor of CDK2, CDK4 or CDK6.

In one embodiment the mammal in the methods and uses of the present invention is a human.

Suitably, the present invention relates to a method of treating or lessening the severity of a cancer that is either wild type or mutant for each of Raf, Ras, MEK, and PI3K/Pten. This includes but is not limited to patients having cancers that are mutant for RAF, wild type for RAS, wild type for MEK, and wild type for PI3K/PTEN; mutant for RAF, mutant for RAS, wild type for MEK, and wild type for PI3K/PTEN; mutant for RAF, mutant for RAS, mutant for MEK, and wild type for PI3K/PTEN; and mutant for RAF, wild type for RAS, mutant for MEK, and wild type PI3K/PTEN.

The term "wild type" as is understood in the art refers to a polypeptide or polynucleotide sequence that occurs in a native population without genetic modification. As is also understood in the art, a "mutant" includes a polypeptide or polynucleotide sequence having at least one modification to an amino acid or nucleic acid compared to the corresponding amino acid or nucleic acid found in a wild type polypeptide or polynucleotide, respectively. Included in the term mutant is Single Nucleotide Polymorphism (SNP) where a single base pair distinction exists in the sequence of a nucleic acid strand compared to the most prevalently found (wild type) nucleic acid strand.

Cancers that are either wild type or mutant for Raf, Ras, MEK, or mutant for PI3K/Pten are identified by known methods. For example, wild type or mutant tumor cells can be identified by DNA amplification and sequencing techniques, DNA and RNA detection techniques, including, but not limited to Northern and Southern blot, respectively, and/or various biochip and array technologies. Wild type and mutant polypeptides can be detected by a variety of techniques including, but not limited to immunodiagnostic techniques such as ELISA, Western blot or immunocyto chemistry. Suitably, Pyrophosphorolysis-activated polymerization (PAP) and/or PCR methods may be used. Liu, Q et al; Human Mutation 23:426-436 (2004).

The following examples are intended for illustration only and are not intended to limit the scope of the invention in any way.

EXAMPLES

Example 1

Capsule Composition

An oral dosage form for administering a combination of the present invention is produced by filing a standard two piece hard gelatin capsule with the ingredients in the proportions shown in Table A, below.

TABLE A

| INGREDIENTS | AMOUNTS |
| --- | --- |
| N-{3-[3-cyclopropyl-5-(2-fluoro-4-iodo-phenylamino)6,8-dimethyl-2,4,7-trioxo-3,4,6,7-tetrahydro-2H-pyrido[4,3-d]pyrimidin-1-yl]phenyl}acetamide hydrochloride (Compound A) | 5 mg |
| N-{3-[5-(2-Amino-4-pyrimidinyl)-2-(1,1-dimethylethyl)-1,3-thiazol-4-yl]-2-fluorophenyl}-2,6-difluorobenzenesulfonamide methanesulfonate (the methanesulfonate salt of Compound B) | 100 mg |
| Mannitol | 250 mg |
| Talc | 125 mg |
| Magnesium Stearate | 8 mg |

While the preferred embodiments of the invention are illustrated by the above, it is to be understood that the invention is not limited to the precise instructions herein disclosed and that the right to all modifications coming within the scope of the following claims is reserved.

Assays

In vitro Combination Studies of BRAF and MEK Inhibitors on Cancer Cells Lines from Multiple Origins Encoding Different Mutations A. Concentration Ranges A Drug combinations experiments were carried out in 384-well plates. Cell were plated in 384-well plates at 500 cells/well in culture media appropriate for each cell type, supplemented with 10% FBS and 1% penicillin/streptomycin, and incubated overnight at 37° C., 5% $CO_2$. Sixteen concentrations of 2 folds dilution of each drug were tested in matrix for cell growth inhibition. Concentrations tested for compound A (free form). were 1 µM-0.03 nM and for compound B (DMSO solvate) were 10 µM-0.3 nM. Cells were treated with compound combination and incubated at 37° C. for 72 hours. Cell growth was measured using CellTiter-Glo® reagent according to the manufacturer's protocol and signals were read on a PerkinElmer EnVision™ reader set for luminescence mode with a 0.5-second read. Results are expressed as a percentage inhibition compared to DMSO treated cells and background correction was made by subtraction of values from wells containing no cells.

The response (percent inhibition compared to untreated samples and normalized to media alone) of compound "A" at "a" concentration (Ra) and that of compound "B" at "b" concentration (Rb) is compared to response of the mixture of compounds "A" and "B" at concentrations "a" and "b" respectively (Rab). Using these values, Excess Over Highest Single Agent (EOHSA) was calculated for each concentration of each of the tested cell lines:
  Rab>10% of the higher value among Ra and Rb=more than additive Rab<-10% of the higher value among Ra and Rb=antagonism Using this formula, if Rab is greater by 10% or more than the highest value between Ra and Rb the drug combination is considered more than additive. If Rab is smaller by 10% or more than the highest value between Ra and Rb the drug combination is antagonistic.

For each of the cell lines tested, the number of combinations in the 16×16 matrix with more than additive response (those where the Rab is greater than 10% higher than the higher value among Ra and Rb) were enumerated. The number of more than additive combinations (out of the 264 tested) are summarized in Table 1. On this table, concentration combinations on a given cell line were found to be particularly beneficial (gray square) if more than 20% (51 combination out of 256 tested) of combinations tested showed >10% EOHSA.

TABLE 1

Combination effect of MEK and BRAF inhibitors on multiple cancer cell lines.

| Origin | cell lines | MAPK | PI3K/PTEN | # of drug combinations w EOHSA (264 combinations evaluated) | % |
|---|---|---|---|---|---|
| Skin | A375P | $BRAF^{V600E}$ | WT/WT | 34 | 13 |
| Colon | RKO | $BRAF^{V600E}$ | mut/WT | 111 | 43 |
| Skin | A101D | $BRAF^{V600E}$ | WT/mut | 26 | 10 |
| Skin | SK-MEL-5 | $BRAF^{V600E}NRAS^{G12V}$ | WT/inc | 40 | 16 |
| Lung | A-549 | $KRAS^{G12S}$ | WT/WT | 49 | 19 |
| Colon | LoVo | $KRAS^{G13D}$ | WT/WT | 71 | 28 |
| Colon | HCT116 | $KRAS^{G13D}$ | mut/WT | 57 | 22 |
| Skin | SK-MEL-2 | $NRAS^{Q61R}$ | WT/WT | 75 | 29 |
| Lung | H1299 | $NRAS^{Q61R}$ | WT/WT | 62 | 24 |
| Sarcoma | HT-1080 | $NRAS^{Q61K}$ | WT/WT | 72 | 28 |
| Breast | MDA-MB-231 | $NRAS^{Q61K}$ | WT/WT | 74 | 29 |

These data demonstrate that the combination of Compound A and Compound B is favourable on multiple cancer cell lines from multiple origins independent of the mutational status of key oncogenes within the MAPK or the AKT/PI3K/PTEN pathways.

B. Concentration Ranges B

Evaluation similar to Section A above of combination of Compound A and Compound B were performed using the data generated in Section A, but only for drug concentrations which were deemed to be clinically relevant (100 nM-3 nM). These concentrations were chosen as those which tended to be efficacious but non-toxic in pre-clinical mice xenograft models. Using these concentrations, a total of 25 drug combinations were evaluated for each cell line, and results are summarized in Table 2.

The number of combinations having Rab>10% of the higher value among Ra and Rb of the 25 clinically relevant combinations tested were calculated and expressed as a percentage in Table 2.

TABLE 2 in vitro combination of MEK and BRAF inhibitors
using clinically relevant drug concentrations

| Origin | cell lines | MAPK | PI3K/PTEN | # of drug combinations w EOHSA at est. clinical concentration (25 combinations evaluated) | % |
|---|---|---|---|---|---|
| Skin | A375P | BRAF$^{V600E}$ | WT/WT | 16 | 64 |
| Colon | RKO | BRAF$^{V600E}$ | mut/WT | 23 | 92 |
| Skin | A101D | BRAF$^{V600E}$ | WT/mut | 17 | 68 |
| Skin | SK-MEL-5 | BRAF$^{V600E}$ NRAS$^{G12V}$ | WT/inc | 21 | 84 |
| Lung | A-549 | KRAS$^{G12S}$ | WT/WT | 17 | 68 |
| Colon | LoVo | KRAS$^{G13D}$ | WT/WT | 6 | 24 |
| Colon | HCT116 | KRAS$^{G13D}$ | mut/WT | 7 | 28 |
| Skin | SK-MEL-2 | NRAS$^{Q61R}$ | WT/WT | 1 | 4 |
| Lung | H1299 | NRAS$^{Q61R}$ | WT/WT | 8 | 32 |
| Sarcoma | HT-1080 | NRAS$^{Q61K}$ | WT/WT | 3 | 12 |
| Breast | MDA-MB-231 | NRAS$^{Q61K}$ | WT/WT | 5 | 20 |

The data demonstrate that the combination of Compound A and Compound B is favourable in most cell lines tested at relevant clinical drug concentrations and highly favourable on all BRAF$^{V600E}$ and KRAS mutant cell lines tested, independent of the PI3K/PTEN pathway mutational status.

In vitro Cell Growth Inhibition in Tumor Cell Lines
Methods:

Cell lines and growth conditions—Human colon tumor lines, Colo-205, DLD-1, HCT-8, HT-29, LS-1034, NCI-H508, RKO, SW1417, SW1463, SW480 and SW837, and human melanoma line A375 were from ATCC. A375 PF11 was derived from A375. 12R5-1, 12R5-3, 12R8-1, 12R8-3, 16R5-2, 16R6-3 and 16R6-4 are single cell clones derived from mixed populations of A375 PF11 cells that were selected to grow in Compound A to concentrations of 1200 and 1600 nM, thereby exhibiting acquired resistance to Compound B. All lines were cultured in RPMI 1640 medium containing 10% fetal bovine serum (FBS).

Cell growth inhibition assay and combination data analysis—All cells were cultured for a minimum of 72 hours prior to cell plating. Cells were assayed in a 96-well tissue culture plate (NUNC 136102) of RPMI medium containing 10% FBS for all cells at 1,000 cells per well. Approximately 24 hours after plating, cells were exposed to ten, three-fold serial dilutions of compound or the combination of the two agents at a constant molar to molar ratio of 1:10 Compound A (DMSO solvate) to Compound B (free form) in RPMI media containing 10% FBS. Concentrations tested for Compound A were 1 µM-0.05 nM and for Compound B were 10 µM-0.5 nM. Cells were incubated in the presence of compounds for 3 days. ATP levels were determined by adding Cell Titer Glo® (Promega) according to the manufacturer's protocol. Briefly, Cell Titer Glo® was added each plate, incubated for 30 minutes then luminescent signal was read on the SpectraMax L plate reader with a 0.5 sec integration time.

Inhibition of cell growth was estimated after treatment with compound or combination of compounds for three days and comparing the signal to cells treated with vehicle (DMSO). Cell growth was calculated relative to vehicle (DMSO) treated control wells. Concentration of compound that inhibits 50% of control cell growth (IC$_{50}$) was interpolated when y=50% of the vehicle control using nonlinear regression with the equation, y=(A+(B−A)/(1+(C/x)^D))), where A is the minimum response (y$_{min}$), B is the maximum response (y$_{max}$), C is the inflection point of the curve (EC$_{50}$) and D is the Hill coefficient.

Combination effects on potency were evaluated using Combination Index (CI) which was calculated with the back-interpolated IC$_{50}$ values and the mutually non-exclusive equation derived by Chou and Talalay (1):

$$CI = Da/IC_{50}(a) + Db/IC_{50}(b) + (Da \times Db)/(IC_{50}(a) \times IC_{50}(b))$$

where IC$_{50}$(a) is the IC$_{50}$ of Compound A; IC$_{50}$(b) is the IC$_{50}$ for Compound B; Da is the concentration of Compound A in combination with Compound B that inhibited 50% of cell growth; and Db is the concentration of Compound B in combination with Compound A that inhibited 50% of cell growth. In general, a CI value <0.9, between 0.9 and 1.1, or >1.1 indicates synergy, additivity and antagonism, respectively. In general, the smaller the CI number, the greater is the strength of synergy.

The combination effects on the response scale were quantified by Excess Over Highest Single Agent (EOHSA) based on the concept of nonlinear blending as described in detail by Peterson and Novick (2007) and Peterson (2010) [(2;3) [Peterson and Novick, 2007; Peterson, 2010]. EOHSA values are defined as increases in improvement (here, in 'percentage points' (ppts) difference) produced by the combination over the best single agent at its component dose level for the combination. For single agent and combination treatments, cells were exposed to compounds at a fixed-dose-ratio, and dose response curves were fit to the experimental data and analyzed using regression models. At specified total dose levels of IC$_{50}$ along the dose response curve, the dose combination (corresponding to IC$_{50}$) was determined for making EOHSA statistical inferences. More specifically, for a combination drug experiment involving drug 1 at dose d1 and drug 2 at dose d2, (i.e., total dose equals d1+d2) is said to have a positive EOHSA if the mean response at the combination is better than the mean response to drug 1 at dose d1 or drug 2 at dose d2.

Results:

The effect of cell growth inhibition by a MEK inhibitor Compound A, a BRAF inhibitor Compound B and their combination was determined in a panel of human tumor cell lines. The mean IC$_{50}$s (from at least two independent experiments) and the combination effects at IC$_{50}$s are summarized in Table 3 with BRAF and KRAS mutation status.

Referring to Table 3, the four colon cell lines with BRAF V600E mutation displayed sensitivity to Compound A with IC$_{50}$ values between 0.001 µM and 0.025 µM, and to Compound B with IC$_{50}$ values between 0.018 M and 5.654 µM. The combination of Compound A and Compound B was synergistic with CI values between 0.25 and 0.73 and/or enhanced cell growth inhibition with EOHSA values between 7 and 26 ppts in these four lines with BRAF V600E mutation. The seven colon lines without BRAF V600E mutation (either with BRAF G596R or KRAS mutations) were insensitive to Compound B (IC$_{50}$>10 µM), however highly sensitive to cell growth inhibition by Compound A with ICsos ranging from 0.001 to 0.093 µM in six out of the seven lines. The combination of Compound A and Compound B showed enhanced cell growth inhibition in DLD1 colon tumor line, and minimal to no added benefit over Compound A single compound treatment in the other six colon cell lines.

For the melanoma lines listed in Table 3, A375 PF11 cells with BRAF V600E mutation were highly sensitive to either Compound A (IC$_{50}$=0.001 µM) or Compound B (IC$_{50}$=0.012 µM) single agent. The combination of Compound A and Compound B were synergistic with CI value of 0.3 in A375 PF11 cells. The melanoma lines 12R8-3, 12R8-1, 12R5-3, and 16R6-3 were resistant to Compound B (IC$_{50}$>10 µM), moderately sensitive to Compound A with IC$_{50}$s ranging from 0.058 µM to 0.109, and responded to the combination of Compound A and Compound B with IC$_{50}$s ranging from 0.018 to 0.023 µM for Compound A and 0.178-0.234 µM for Compound B.

The melanoma lines 16R5-2, 16R6-4 and 12R5-1 were resistant or insensitive to either Compound A or Compound B alone, however became sensitive to the combination of Compound A and Compound B with $IC_{50}$s ranging from 0.018 to 0.039 μM for Compound A and 0.177-0.386 μM for Compound B. The combination of Compound A and Compound B also showed enhancement of cell growth inhibition in all these melanoma lines. Note, CI values could not be calculated therefore not applicable where the single agent values were outside of the range tested.

Of interest, the combined administration of Compound A and Compound B in the BRAF-V600E mutant colon and melanoma cell lines showed synergistic effect demonstrated by the CI values <0.9, or resulted in a reduced $IC_{50}$ value comparing to that of Compound A or Compound B, administered alone, where at least one of the single agents did not result in 50% inhibition within the tested range.

allowed to establish. Dosing began on day 24 after implantation, corresponding to a mean tumor volume of ~200 mm³.

This human xenograft tumor model utilized 4 groups of mice, with 8 mice per group. The animals were identified via a subcutaneous (sc) microchip or tattoos.

A first group of untreated or placebo-treated tumor-bearing control animals acted as controls. A second group was dosed once daily orally with N-{3-[5-(2-Amino-4-pyrimidinyl)-2-(1,1-dimethylethyl)-1,3-thiazol-4-yl]-2-fluorophenyl}-2,6-difluorobenzenesulfonamide (crystalline free base form) (Compound B). A third group was dosed once daily orally with N-{3-[3-cyclopropyl-5-(2-fluoro-4-iodo-phenylamino)6,8-dimethyl-2,4,7-trioxo-3,4,6,7-tetrahydro-2H-pyrido[4,3-d]pyrimidin-1-yl]phenyl}acetamide dimethyl sulfoxide solvate (Compound A). A fourth group was dosed once daily orally with a combination of N-{3-[5-(2-Amino-4-pyrimidi-

TABLE 3

Cell growth inhibition by Compound A, Compound B and their combination in human tumor cell lines.

| | | $IC_{50}$ values in micromolar (mean ± std) | | | | | |
|---|---|---|---|---|---|---|---|
| | | Single Agent | | Compound A or B = 1:10 molar ratio combination | | Combination Effects at $IC_{50}$ | |
| Tumor Cell Lines | Mutation Status KRAS/BRAF | Compound A | Compound B | Compound A | Compound B | CI | EOHSA (ppt) |
| Colon Colo-205 | BRAF_V600E | 0.001 ± 0.000 | 0.018 ± 0.013 | 0.0005 ± 0.0002 | 0.005 ± 0.002 | 0.69 ± 0.10 | 26 ± 10.6 |
| HT-29 | BRAF_V600E | 0.001 ± 0.001 | 0.022 ± 0.022 | 0.0004 ± 0.0003 | 0.004 ± 0.003 | 0.73 ± 0.11 | 15 ± 4.3 |
| SW1417 | BRAF_V600E | 0.003 ± 0.002 | 0.203 ± 0.015 | 0.001 ± 0.0003 | 0.014 ± 0.003 | 0.69 ± 0.44 | 7 ± 8.1 |
| RKO | BRAF_V600E | 0.025 ± 0.007 | 5.654 ± 3.900 | 0.006 ± 0.001 | 0.057 ± 0.015 | 0.25 ± 0.01 | 18 ± 2.7 |
| DLD1 | KRAS_G13D | 0.557 ± 0.393 | >10 | 0.044 ± 0.020 | 0.443 ± 0.030 | N/A | 22 ± 2.3 |
| HCT-8 | KRAS_G13D | 0.050 ± 0.011 | >10 | 0.035 ± 0.013 | 0.348 ± 0.132 | N/A | 7 ± 2.9 |
| SW480 | KRAS_G12C | 0.042 ± 0.003 | >10 | 0.024 ± 0.003 | 0.235 ± 0.034 | N/A | 5 ± 0.7 |
| NCI-H508 | BRAF_G596R | 0.010 ± 0.005 | >10 | 0.008 ± 0.005 | 0.081 ± 0.054 | N/A | 4 ± 4.1 |
| SW837 | KRAS_G12C | 0.093 ± 0.063 | >10 | 0.087 ± 0.037 | 0.874 ± 0.368 | N/A | 0 ± 2.8 |
| LS-1034 | KRAS_A146T | 0.011 ± 0.007 | >10 | 0.029 ± 0.022 | 0.295 ± 0.221 | N/A | −21 ± 2.7 |
| SW1463 | KRAS_G12C | 0.005 ± 0.004 | >10 | 0.021 ± 0.013 | 0.210 ± 0.133 | N/A | −26 ± 4.2 |
| Melanoma A375PF11 | BRAF_V600E | 0.001 ± 0.001 | 0.012 ± 0.012 | 0.0002 ± 0.000 | 0.002 ± 0.003 | 0.30 ± 0.32 | 18 ± 3.0 |
| 12R8-1 | BRAF_V600E | 0.058 ± 0.030 | >10 | 0.019 ± 0.017 | 0.186 ± 0.173 | N/A | 22 ± 0.2 |
| 12R8-3 | BRAF_V600E | 0.059 ± 0.037 | >10 | 0.018 ± 0.018 | 0.178 ± 0.182 | N/A | 27 ± 0.7 |
| 12R5-3 | BRAF_V600E | 0.092 ± 0.052 | >10 | 0.021 ± 0.015 | 0.210 ± 0.153 | N/A | 30 ± 5.8 |
| 16R6-3 | BRAF_V600E | 0.109 ± 0.022 | >10 | 0.023 ± 0.021 | 0.234 ± 0.210 | N/A | 25 ± 6.8 |
| 16R5-2 | BRAF_V600E | >1 | >10 | 0.018 ± 0.013 | 0.177 ± 0.128 | N/A | 35 ± 2.1 |
| 16R6-4 | BRAF_V600E | >1 | >10 | 0.021 ± 0.013 | 0.215 ± 0.135 | N/A | 44 ± 12.4 |
| 12R5-1 | BRAF_V600E | >1 | >10 | 0.039 ± 0.021 | 0.386 ± 0.211 | N/A | 61 ± 14.9 |

Table 3 Key:
$IC_{50}$: the concentration of Compound as single agent, or the concentration of Compound A or B in combination when Compound A and Compound B = 1:10 molar ratio that reduces cell growth by 50%;
CI; Combination Index;
N/A = not applicable
EOHSA: Excess over Highest Single Agent, measured as a percentage.

Reference List
(1) Chou T C, Talalay P. Quantitative analysis of dose-effect relationships: the combined effects of multiple drugs or enzyme inhibitors. Adv Enzyme Regul 1984; 22:27-55.
(2) Peterson J J, Novick S J. Nonlinear blending: a useful general concept for the assessment of combination drug synergy. J Recept Signal Transduct Res 2007; 27(2-3):125-46.
(3) Peterson J. A Review of Synergy Concepts of Nonlinear Blending and Dose-Reduction Profiles. Frontiers of Bioscience S2, 483-503. 2010.

Mouse Xenograft Model A

A xenograft models using A375P F11 (human melanoma cell line encoding BRaf$^{V600E}$ mutation) cells were established from cells grown in tissue culture and harvested aseptically using a trypsin digest. The tumor cells were injected subcutaneously into female athymic mice (strain nu/nu) with between 5×10⁶ and 10⁷ cells in 50% martigel. Tumors were nyl)-2-(1,1-dimethylethyl)-1,3-thiazol-4-yl]-2-fluorophenyl}-2,6-difluorobenzenesulfonamide (crystalline free base form) and N-{3-[3-cyclopropyl-5-(2-fluoro-4-iodo-phenylamino)6,8-dimethyl-2,4,7-trioxo-3,4,6,7-tetrahydro-2H-pyrido[4,3-d]pyrimidin-1-yl]phenyl}acetamide dimethyl sulfoxide solvate. Each drug was provided in a suspension of 0.5% HPMC/0.2% TWEEN 80.

The tumor sizes were measured twice weekly using Vernier callipers. Tumor volume was calculated from two-dimensional measurements using an equation approximating the volume of a prolate ellipsoid:

$$\text{Tumor volume in cubic mm} = (\text{length} \times \text{width}^2) \times 0.5$$

The measurements are reported in FIG. 1 following 36 day treatment. The data showed that combination of the MEK and B-Raf inhibitors is advantageous compared to each agent administrated individually.

Mouse Xenograft Model B

A375P cells were harvested from culture flasks by exposure to 0.25% trypsin/EDTA for 5 min at 37° C. Detached cells were collected, centrifuged (1500 rpm, 5 min, 4° C.) and rinsed to remove the trypsin solution. Cells were resuspended in PBS without magnesium or calcium and counted. Cells were spun as previously to remove PBS and a single cell suspension was created either in 50% Matrigel: 50% PBS (v:v) or 100% PBS so that a 100 μL subcutaneous injection would deliver the required number of cells per mouse. The A375P melanoma line was injected with Matrigel at 1.75 million cells per mouse subcutaneously into 8-10 week old, female CD-1 nu/nu mice. Tumors were established (~150-300 mm³) for all cell lines within 2-4 weeks post-injection.

Compound A (DMSO solvate) and Compound B (free form) were administered orally to mice at the indicated doses in 0.2 ml/20 gram body weight in 0.5% HPMC (hydroxypropylmethylcellulose, Sigma cat #H7509) and 0.2% Tween 80 (Sigma cat #P1754) in distilled water, pH 7.0-8.0.

Figure 2:
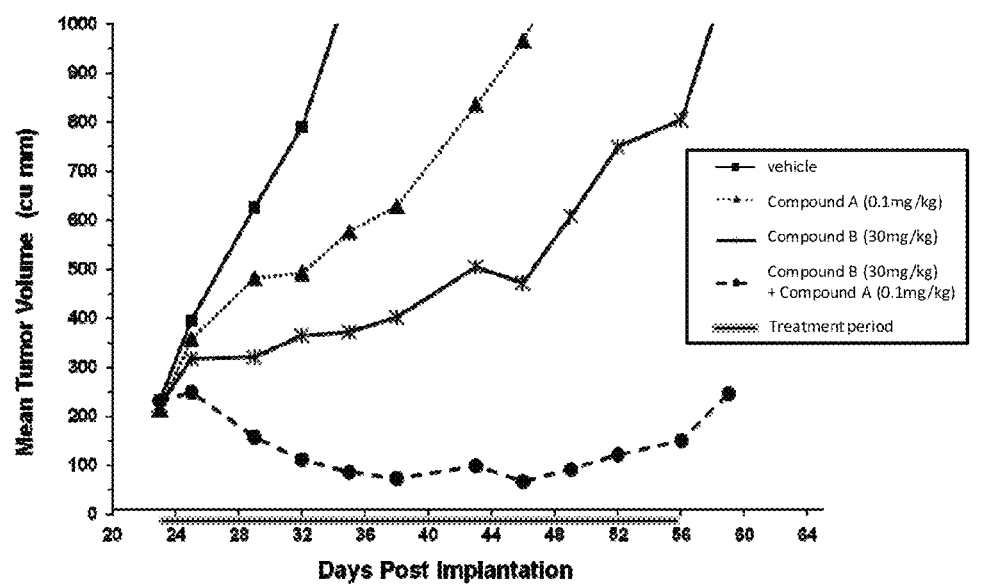
FIG. 2 is a graph showing the tumor growth inhibition due to administration of the MEK inhibitor of Compound A, the B-Raf inhibitor of Compound B, and the combination thereof.

Mice with similar sized tumors (150-200 mm³) were identified. The length and width of tumors were measured by handheld calipers and body weights of mice were measured using a bench top weighing scale. Mice were placed in groups of eight or seven accordingly and dosed orally with either vehicle, individual compound or compound combination. Mice were weighed and tumors measured twice weekly for the duration of the study. Data presented in FIG. 2 demonstrates that combination of Compound A (0.1 mg/kg) and Compound B (30 mg/kg) daily for 33 days (days 24 to 56 after implantation) is more efficacious than each agent alone.

We claim:

1. A method of treating non-small cell lung cancer in a human in need thereof which comprises the administration of a therapeutically effective amount of
    (i) a compound of formula (I)

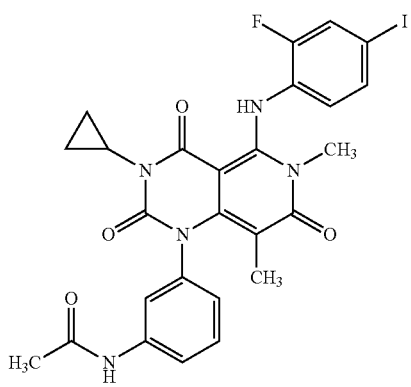

or a pharmaceutically acceptable salt or solvate thereof; and (ii) a compound of formula (II)

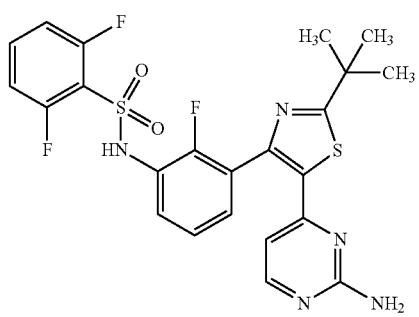

or a pharmaceutically acceptable salt thereof.

2. The method of claim 1, wherein compound (I) is in the form of the dimethyisulfoxide solvate.

3. The method of claim 1, wherein compound (II) is in the form of the methanesulfonate salt.

4. The method of claim 1, wherein the non-small cell lung cancer is BRAF V600E mutant non-small cell lung cancer.

5. A method of treating non-small cell lung cancer in a human in need thereof which comprises the administration of a therapeutically effective amount of
    (i) a compound of formula (I)

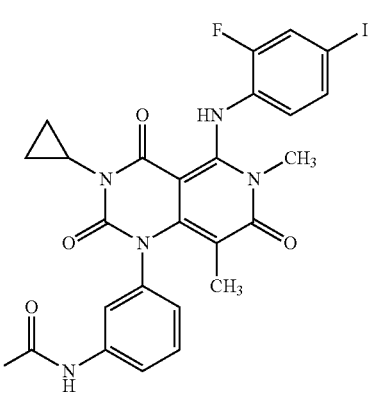

or a pharmaceutically acceptable salt thereof; and
    (ii) a compound of formula (II)

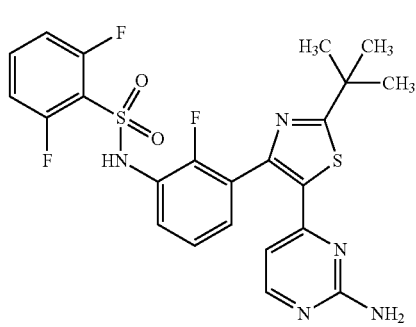

or a pharmaceutically acceptable salt thereof.

* * * * *